United States Patent
Furfine et al.

(10) Patent No.: US 12,331,099 B2
(45) Date of Patent: *Jun. 17, 2025

(54) VEGF ANTAGONIST FORMULATIONS SUITABLE FOR INTRAVITREAL ADMINISTRATION

(71) Applicant: Regeneron Pharmaceuticals, Inc., Tarrytown, NY (US)

(72) Inventors: Eric Furfine, Concord, MA (US); Daniel Dix, LaGrangeville, NY (US); Kenneth Graham, Pleasant Valley, NY (US); Kelly Frye, Mendham, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/924,707

(22) Filed: Oct. 23, 2024

(65) Prior Publication Data
US 2025/0042972 A1 Feb. 6, 2025

Related U.S. Application Data

(60) Continuation of application No. 18/344,786, filed on Jun. 29, 2023, which is a continuation of application No. 17/348,438, filed on Jun. 15, 2021, now Pat. No. 11,732,024, which is a continuation of application No. 16/582,486, filed on Sep. 25, 2019, now Pat. No. 11,066,458, which is a continuation of application No. 16/159,269, filed on Oct. 12, 2018, now Pat. No. 10,464,992, which is a continuation of application No. 15/879,294, filed on Jan. 24, 2018, now Pat. No. 10,400,025, which is a continuation of application No. 15/095,606, filed on Apr. 11, 2016, now Pat. No. 9,914,763, which is a continuation of application No. 14/330,096, filed on Jul. 14, 2014, now Pat. No. 9,340,594, which is a continuation of application No. 13/914,996, filed on Jun. 11, 2013, now Pat. No. 8,802,107, which is a continuation of application No. 13/329,770, filed on Dec. 19, 2011, now Pat. No. 8,481,046, which is a continuation of application No. 12/833,417, filed on Jul. 9, 2010, now Pat. No. 8,092,803, which is a continuation of application No. 12/560,885, filed on Sep. 16, 2009, now Pat. No. 7,807,164, which is a division of application No. 11/818,463, filed on Jun. 14, 2007, now Pat. No. 7,608,261.

(60) Provisional application No. 60/814,484, filed on Jun. 16, 2006.

(51) Int. Cl.
| | | |
|---|---|---|
| A61K 38/17 | (2006.01) | |
| A61K 9/00 | (2006.01) | |
| A61K 9/19 | (2006.01) | |
| A61K 47/02 | (2006.01) | |
| A61K 47/10 | (2017.01) | |
| A61K 47/26 | (2006.01) | |
| A61M 5/178 | (2006.01) | |
| C07K 14/47 | (2006.01) | |
| C07K 14/71 | (2006.01) | |

(52) U.S. Cl.
CPC ............ *C07K 14/71* (2013.01); *A61K 9/0019* (2013.01); *A61K 9/0048* (2013.01); *A61K 9/19* (2013.01); *A61K 38/179* (2013.01); *A61K 38/1793* (2013.01); *A61K 47/02* (2013.01); *A61K 47/10* (2013.01); *A61K 47/26* (2013.01); *A61M 5/178* (2013.01); *C07K 14/47* (2013.01); *C07K 14/4705* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,399,670 A | 3/1995 | Bhattacharya et al. |
| 5,656,730 A | 8/1997 | Lee |
| 5,763,401 A | 6/1998 | Nayar et al. |
| 5,851,999 A | 12/1998 | Ulrich et al. |
| 6,011,003 A | 1/2000 | Charnock-Jones et al. |
| 6,100,071 A | 8/2000 | Davis-Smyth et al. |
| 6,171,586 B1 | 1/2001 | Lam et al. |
| 6,267,958 B1 | 7/2001 | Andya et al. |
| 6,270,993 B1 | 8/2001 | Shibuya et al. |
| 6,436,897 B2 | 8/2002 | Danko et al. |
| 6,472,179 B2 | 10/2002 | Stahl et al. |

(Continued)

FOREIGN PATENT DOCUMENTS

| | | |
|---|---|---|
| CA | 2372053 | 11/2000 |
| CA | 2569108 A1 | 12/2005 |

(Continued)

OTHER PUBLICATIONS

Andersen, "Determination of specific proteins by the FIA principle," Journal of *Automatic Chemistry*, 12(2):53-59 (Mar.-Apr. 1990).

(Continued)

*Primary Examiner* — Christine J Saoud
*Assistant Examiner* — Jon M Lockard
(74) *Attorney, Agent, or Firm* — Arnold & Porter Kaye Scholer LLP

(57) ABSTRACT

Ophthalmic formulations of a vascular endothelial growth factor (VEGF)-specific fusion protein antagonist are provided suitable for intravitreal administration to the eye. The ophthalmic formulations include a stable liquid formulation and a lyophilizable formulation. Preferably, the protein antagonist has an amino acid sequence of SEQ ID NO:4.

30 Claims, No Drawings
Specification includes a Sequence Listing.

(56) References Cited

U.S. PATENT DOCUMENTS

| | | |
|---|---|---|
| 6,676,941 B2 | 1/2004 | Thorpe et al. |
| 6,777,429 B1 | 8/2004 | Adam et al. |
| 6,833,349 B2 | 12/2004 | Xia et al. |
| 6,875,432 B2 | 4/2005 | Liu et al. |
| 6,884,879 B1 | 4/2005 | Baca et al. |
| 6,897,294 B2 | 5/2005 | Davis-Smyth et al. |
| 7,001,892 B1 | 2/2006 | Chmielweski et al. |
| 7,033,604 B2 | 4/2006 | Ueno |
| 7,052,691 B2 | 5/2006 | Sleeman et al. |
| 7,060,268 B2 | 6/2006 | Andya et al. |
| 7,070,959 B1 | 7/2006 | Papadopoulos et al. |
| 7,087,411 B2 | 8/2006 | Daly et al. |
| 7,303,747 B2 | 12/2007 | Wiegand et al. |
| 7,374,757 B2 | 5/2008 | Papadopoulos et al. |
| 7,374,758 B2 | 5/2008 | Papadopoulos et al. |
| 7,482,002 B2 | 1/2009 | Cedarbaum |
| 7,608,261 B2 | 10/2009 | Furfine et al. |
| 7,750,138 B2 | 7/2010 | Fang et al. |
| 7,807,164 B2 | 10/2010 | Furfine et al. |
| 7,951,585 B2 | 5/2011 | Kc |
| 8,084,234 B2 | 12/2011 | Papadopoulos et al. |
| 8,092,803 B2 | 1/2012 | Furfine et al. |
| 8,110,546 B2 | 2/2012 | Dix et al. |
| 8,216,575 B2 | 7/2012 | Yu |
| 8,343,737 B2 | 1/2013 | Papadopoulos et al. |
| 8,404,638 B2 | 3/2013 | Dix et al. |
| 8,481,046 B2 | 7/2013 | Furfine et al. |
| 8,647,842 B2 | 2/2014 | Papadopoulos et al. |
| 8,710,004 B2 | 4/2014 | Dix et al. |
| 8,802,107 B2 | 8/2014 | Furfine et al. |
| 8,921,316 B2 | 12/2014 | Dix et al. |
| 9,340,594 B2 | 5/2016 | Furfine et al. |
| 9,416,167 B2 | 8/2016 | Dix et al. |
| 9,511,140 B2 | 12/2016 | Dix et al. |
| 9,580,489 B2 | 2/2017 | Furfine et al. |
| 9,636,400 B2 | 5/2017 | Dix et al. |
| 9,657,084 B2 | 5/2017 | Kc et al. |
| 9,914,763 B2 | 3/2018 | Furfine et al. |
| 10,400,025 B2 | 9/2019 | Furfine et al. |
| 10,406,226 B2 | 9/2019 | Dix et al. |
| 10,464,992 B2 | 11/2019 | Furfine et al. |
| 10,857,231 B2 | 12/2020 | Dix et al. |
| 11,066,458 B2 | 7/2021 | Furfine et al. |
| 11,084,865 B2 | 8/2021 | Furfine et al. |
| 2001/0014326 A1 | 8/2001 | Andya et al. |
| 2002/0004478 A1 | 1/2002 | Danko et al. |
| 2003/0092606 A1 | 5/2003 | L'Italien et al. |
| 2003/0113316 A1 | 6/2003 | Kaisheva et al. |
| 2003/0138417 A1 | 7/2003 | Kaisheva et al. |
| 2003/0143697 A1 | 7/2003 | Stahl et al. |
| 2003/0202972 A1 | 10/2003 | Andya et al. |
| 2004/0014667 A1 | 1/2004 | Daly et al. |
| 2004/0170623 A1 | 9/2004 | Arvinte et al. |
| 2004/0197324 A1 | 10/2004 | Liu et al. |
| 2004/0213787 A1 | 10/2004 | Sleeman et al. |
| 2004/0265309 A1 | 12/2004 | Kandel et al. |
| 2004/0266688 A1 | 12/2004 | Nayak |
| 2005/0004027 A1 | 1/2005 | Wiegand et al. |
| 2005/0032699 A1 | 2/2005 | Holash et al. |
| 2005/0043236 A1 | 2/2005 | Daly et al. |
| 2005/0112061 A1 | 5/2005 | Holash et al. |
| 2005/0175610 A1 | 8/2005 | Wiegand et al. |
| 2005/0245447 A1 | 11/2005 | Papadopoulos et al. |
| 2005/0250737 A1 | 11/2005 | Hughes et al. |
| 2005/0260203 A1 | 11/2005 | Wiegand |
| 2005/0276808 A1 | 12/2005 | Cedarbaum |
| 2005/0281822 A1 | 12/2005 | Cedarbaum et al. |
| 2005/0281831 A1 | 12/2005 | Davis-Smyth et al. |
| 2006/0008415 A1 | 1/2006 | Kaisheva et al. |
| 2006/0030000 A1 | 2/2006 | Alitalo et al. |
| 2006/0030529 A1 | 2/2006 | Wiegand et al. |
| 2006/0040852 A1 | 2/2006 | Dix et al. |
| 2006/0058234 A1 | 3/2006 | Daly et al. |
| 2006/0217311 A1 | 9/2006 | Dix et al. |
| 2007/0293432 A1 | 12/2007 | Furfine et al. |
| 2008/0085276 A1 | 4/2008 | Wiegand et al. |
| 2009/0264358 A1 | 10/2009 | Yu et al. |
| 2012/0101035 A1 | 4/2012 | Dix et al. |
| 2012/0178683 A1 | 7/2012 | Dix et al. |
| 2013/0261056 A1 | 10/2013 | Dix et al. |
| 2014/0012227 A1 | 1/2014 | Sigg et al. |
| 2015/0079087 A1 | 3/2015 | Dix et al. |
| 2016/0144025 A1 | 5/2016 | Vitti et al. |
| 2016/0175439 A1 | 6/2016 | Dix et al. |
| 2017/0073407 A1 | 3/2017 | Dix et al. |
| 2017/0360930 A1 | 12/2017 | Dix et al. |
| 2020/0390693 A1 | 12/2020 | Kim et al. |

FOREIGN PATENT DOCUMENTS

| | | |
|---|---|---|
| CA | 2598711 | 10/2006 |
| CN | 1304427 C | 3/2007 |
| CN | 100502945 C | 6/2009 |
| CN | 100567325 C | 12/2009 |
| CN | 102233132 B | 10/2013 |
| CN | 102380096 B | 4/2014 |
| CN | 103212075 B | 6/2017 |
| CN | 107115294 A | 9/2017 |
| EP | 3753548 | 12/2020 |
| EP | 2944306 | 1/2021 |
| JP | H10273450 | 10/1998 |
| JP | 11510170 | 9/1999 |
| JP | 2002516871 | 6/2002 |
| KR | 10-1861163 | 5/2018 |
| KR | 102494021 | 2/2023 |
| WO | WO 1989/011298 A1 | 11/1989 |
| WO | WO 1993/000807 | 1/1993 |
| WO | WO 1994/007510 | 4/1994 |
| WO | WO 1997/004801 A1 | 2/1997 |
| WO | WO 1997/26909 A1 | 7/1997 |
| WO | WO 1997/044453 A1 | 11/1997 |
| WO | WO 1998/045331 A2 | 10/1998 |
| WO | WO 1999/013909 | 3/1999 |
| WO | WO 1999/062536 | 12/1999 |
| WO | WO 2000/063380 A1 | 10/2000 |
| WO | WO 2000/075319 | 12/2000 |
| WO | WO 2002/060489 | 8/2002 |
| WO | WO 2003/072060 A2 | 9/2003 |
| WO | WO 2004/087206 A2 | 10/2004 |
| WO | WO 2004/091658 | 10/2004 |
| WO | WO 2004/103159 | 12/2004 |
| WO | WO 2004/106378 | 12/2004 |
| WO | WO 2005/000895 | 1/2005 |
| WO | WO 2005/000900 | 1/2005 |
| WO | WO 2005011734 | 2/2005 |
| WO | WO 2005/020972 | 3/2005 |
| WO | WO 2005/072772 | 8/2005 |
| WO | WO 2005/102303 A2 | 11/2005 |
| WO | WO2006/015297 | 2/2006 |
| WO | WO 2006/023665 A2 | 3/2006 |
| WO | WO 2006/047325 | 5/2006 |
| WO | WO 2006/088650 | 8/2006 |
| WO | WO 2006/104852 | 10/2006 |
| WO | WO 2006/138181 A2 | 12/2006 |
| WO | WO 2007/112675 | 10/2007 |
| WO | WO 2007/149334 | 12/2007 |
| WO | WO 2008121665 A1 | 10/2008 |
| WO | WO 2008134644 A1 | 11/2008 |
| WO | WO 2010125416 A1 | 11/2010 |
| WO | WO 2017/129685 A1 | 8/2017 |
| WO | WO 2018/094316 A1 | 5/2018 |
| WO | WO 2018/199408 A1 | 11/2018 |

OTHER PUBLICATIONS

Declaration of Alexander M. Klibanov, Ph.D., dated Apr. 25, 2023, filed in IPR2023-00462.
Declaration of Alexander M. Klibanov, Ph.D., dated Nov. 2, 2023, filed in IPR2023-00462.
Declaration of Dr. Alpaslan Yaman dated Nov. 20, 2024, filed in IPR2025-00176.
Declaration of Dr. Edward Chaum dated Nov. 15, 2024, in IPR2025-00176.

(56) References Cited

OTHER PUBLICATIONS

Declaration of Dr. Michael Butler dated Nov. 18, 2024, in IPR2025-00176.
Declaration of Dr. Peter Tessier in Support of Petition for Inter Partes Review of U.S. Pat. No. 11,084,865 dated Jan. 14, 2025, in IPR2025-00456.
Ejima et al., "Arginine as an effective additive in gel permeation chromatography," *Journal of Chromatography A*, 1094:49-55 (available online Oct. 5, 2005).
Gandhi et al., "Some Lessons Learned From a Comparison Between Sedimentation Velocity Analytical Ultracentrifugation and Size Exclusion Chromatography to Characterize and Quantify Protein Aggregates," *Journal of Pharmaceutical Sciences*, 106:2178-2186 (Aug. 2017) (available online May 4, 2017).
Mahler et al., "Induction and analysis of aggregates in a liquid IgG1-antibody formulation," *European Journal of Pharmaceutics and Biopharmaceutics*, 59:407-417 (available online Jan. 19, 2005).
Mimura et al., "The influence of glycosylation on the thermal stability and effector function expression of human IgG1-Fc: properties of a series of truncated glycoforms," *Molecular Immunology*, 37:697-706 (Aug./Sep. 2000).
Panka, "Glycosylation is Influential in Murine IgG3 Self-Association," *Molecular Immunology*, 34(8/9):593-598 (Jun. 1997).
Petition for Inter Partes Review of U.S. Pat. No. 11,084,865 filed Jan. 15, 2025 in IPR 2025-00456.
Petition for Inter Partes Review of U.S. Pat. No. 11,084,865 filed Nov. 20, 2024 in IPR 2025-00176.
Testimony of Kenneth S. Graham, Ph.D., on Jun. 21, 2023, in *Regeneron Pharmaceuticals, Inc. v. Mylan Pharmaceuticals, Inc. et al.*, Civil Action No. 1:22-cv-61 (ND WVa 2024).
Yumioka et al., "Mobile Phase Containing Arginine Provides More Reliable SEC Condition for Aggregation Analysis," *Journal of Pharmaceutical Sciences*, 99(2):618-620 (Feb. 2010).
Notice of Judgment in a Civil Action, *Regeneron Pharmaceuticals, Inc. v. Mylan Pharmaceuticals, Inc. et al.*, Civil Action No. 1:22-cv-61, United States District Court for the Norther District of West Virginia, 1 p. (Dec. 27, 2023).
Memorandum Opinion and Order Following Bench Trial (redacted), *Regeneron Pharmaceuticals, Inc. v. Mylan Pharmaceuticals Inc. et al.*, Civil No. 1:22-CV-61 (ND WVa 2024).
*Regeneron Pharmaceuticals, Inc. v. Mylan Pharmaceuticals Inc. et al.*, Case No. 24-2009, Dkt. 67 (Fed. Cir. Jan. 29, 2005).
*Regeneron Pharmaceuticals, Inc. v. Mylan Pharmaceuticals Inc. et al.*, Case No. 24-1965, Dkt. 76 (Fed. Cir. Jan. 29, 2025).
Decision—Adverse Judgment After Institution of Trial, *Celltrion, Inc. et al. v. Regeneron Pharmaceuticals, Inc.*, IPR2023-00462 (Feb. 21, 2024).
4.1.3. Buffer solutions, European Pharmacopoeia 5.0, 431-434 (2004).
Abelson et al., "ADM: New therapies, New mechanisms," *Review of Ophthalmology*, 4 pp. (Jul. 1, 2004).
Akers, "Parenteral Preparations," in *Remington: The Science and Practice of Pharmacy*, Martin (ed), Remington (21st ed) Ch. 41, pp. 802-836 (Lippincott Williams & Wilkins) (May 15, 2005).
Alon et al., "Vascular endothelial growth factor acts as a survival factor for newly formed retinal vessels and has implications for retinopathy of prematurity," *Nature Medicine*, 1(10):1024-1028 (Oct. 1995).
Amand et al., "Controllability analysis of protein glycosylation in CHO cells," *PLOS One*, 9, e87943, 2014 (16 pages).
Amersham Biosciences, Antibody Purification Handbook, 18-1037-46, pp. 5-107 (2002).
AMEVIVE® Label (Issued Sep. 2005) (2 pp.).
Amin et al., "Lyophilization of Polyethylene Glycol Mixtures," *Journal of Pharmaceutical Sciences*, 93(9):2244-2249 (2004).
Andersen et al., "Recombinant protein expression for therapeutic applications," *Current Opinion in Biotechnology*, 13:117-123 (2002).
Andya et al., "Mechanisms of Aggregate Formation and Carbohydrate Excipient Stabilization of Lyophilized Humanized Monoclonal Antibody Formulations," *AAPS PharmSci*, 5(2): Article 10, pp. 1-11 (Apr. 2003).
Anguita et al., "A Review of Aflibercept Treatment for Macular Disease," *Ophthalmol. Ther.*, 10:413-428 (2021).
Annex 1 (D21), filed in Opposition to European Patent No. 2 944 306 B1, 1 pg. (2021).
Anonymous, "Sterile Dosage Forms and Delivery Systems," *Ansel's Pharmaceutical Dosage Forms and Drug Delivery Systems*, 8th ed., Allen, Jr. et al. (eds.), Lippincott Williams & Wilkins, Philadelphia, PA, Section VII, pp 443-505 (2005).
Anonymous, "Lucentis in the treatment of neovascular (wet) age-related macular degeneration (AMD)," EMEA, 1-54 (2007).
Application for Extension of Patent Term Under 35 U.S.C. § 156 filed Dec. 22, 2011, in U.S. Pat. No. 7,374,758 (198 pp.).
Application Note, "Rapid optimisation and development of an automated two-step purification procedure for monoclonal IgG antibodies," Amersham Biosciences, 18-1128-93, 6 pp. (1998).
Arakawa et al., "Protein-Solvent Interactions in Pharmaceutical Formulations," *Pharmaceuticals Research*, 8(3):285-291 (1991).
ARANESP® Prescribing Information (Revised Jun. 2011) (41 pp.).
Aruffo et al., "Immunoglobulin Fusion Proteins," in *Antibody Fusion Proteins*, Chamow et al. (eds.), Wiley-Liss (a John Wiley & Sons, Inc. publication), New York, NY, Chapter 8, pp. 221-241 (Apr. 13, 1999).
Atkinson et al., "Formulation Strategies for Biopharmaceuticals Enduring Success to Market," *The Investigational Drugs Journal*, 4(5):557-560 (2001).
Avastin, Summary of Product Characteristics in Dutch, 2 pp., with English machine translation (2 pp.), as submitted in related Netherlands Impeachment proceeding C/09/675574 and C/09/675547 on Feb. 5, 2025.
Avastin, Summary of Product Characteristics in Dutch, 2 pp., with English machine translation (2 pp.), dated Sep. 2, 2010, as submitted in related Netherlands Impeachment proceeding C/09/675574 and C/09/675547 on Feb. 5, 2025.
Avastin, Summary of Product Characteristics in Dutch, 2 pp., with English machine translation (2 pp.), dated Oct. 26, 2012, as submitted in related Netherlands Impeachment proceeding C/09/675574 and C/09/675547 on Feb. 5, 2025.
Avastin® (Bevacizumab) Drug Approval Package, NDA #12508, https://www.accessdata.fda.gov/drugsatfda_docs/nda/2004/STN-125085_Avastin.cfm, 2 pp. (created Mar. 8, 2005).
Avastin® (Bevacizumab) label, Center for Drug Evaluation and Research Approval Package for: Application No. STN-125085/0, pp. 1-28 (2004).
AVASTIN® (bevacizumab), Highlights of Prescribing Information, US BL 125085 Supplement, 26 pp. (revised: Sep. 2011).
Avastin® (Bevacizumab), Information for healthcare professionals, 26 pp., Dec. 2022 (in German), with 26 page English translation.
AVASTIN® label, as submitted to the USPTO on Jan. 7, 2021, in Inter Partes Review No. IPR2021-00402 (2017) (37 pp.).
Avastin® Prescribing Information, 27 pp. (2004).
Avery et al., "Intravitreal Bevacizumab (Avastin) in the Treatment of Proliferative Diabetic Retinopathy," *Ophthalmology*, 113(10):1695-1705 and 1705e1-e6 (Oct. 2006).
Avery et al., "Intravitreal Bevacizumab (Avastin) for Neovascular Age-Related Macular Degeneration," *American Academy of Ophthalmology*, 113(3):363-372.e5 (Feb. 2006).
Avery, "Regression Of Retinal And Iris Neovascularization After Intravitreal Bevacizumab (Avastin) Treatment," *Retina*, 26(3):352-354, (Mar. 2006).
Back et al., "Increased Thermal Stability of Proteins in the Presence of Sugars and Polyols," *Biochemistry*, 18(23):5191-5196 (1979).
Baffert et al., "Age-Related Changes in Vascular Endothelial Growth Factor Dependency and Angiopoietin-1-Induced Plasticity of Adult Blood Vessels," *Circulation Research*, 984-992 (2004).
Baker et al., "Metabolic Control of Recombinant Protein N-Glycan Processing in NS0 and CHO Cells," *Biotechnol. Bioeng.*, 73(3):188-202 (ebook Published May 5, 2001).

(56) References Cited

OTHER PUBLICATIONS

Bakri et al., "Antiangiogenic Agents: Intravitreal Injection," in *Intraocular Drug Delivery*, G. Jaffe et al. (eds), Ch. 5, pp. 71-84 (Taylor & Francis) (ebook published Mar. 12, 2006).

Bakri et al., "Intravitreal preservative-free triamcinolone acetonide for the treatment of macular oedema," *Eye*, 19:686-688 (published online Aug. 27, 2004).

Bashshur et al., "Intravitreal Bevacizumab for Treatment of Neovascular Age-related Macular Degeneration: A One-year Prospective Study," *Am. J. Ophthalmology*, 145(2):249-256, and 256.e1-256.e2 (Feb. 2008).

Bendtsen et al., "Improved Prediction of Signal Peptides: SignalP 3.0," *J. Mol. Biol.*, 340(4):783-795 (Available online Jun. 9, 2004).

Bernauer et al., "Phosphates in ophthalmological preparations," *Ophthalmologist*, 103:416-417 (2006).

Bettini et al., "Enantioselective Discrimination of Histidine by Means of an Achiral Cubane-Bridged Bis-Porphyrin." *Langmuir*, 37:13882-13889 (Epub Nov. 16, 2021).

Blobel et al., "Transfer of Proteins Across Membranes. I. Presence of proteolytically processed and unprocessed nascent immunoglobulin light chains on membrane-bound ribosomes of murine myeloma," *The Journal of Cell Biology*, 67:835-851 (Dec. 1975).

Bogard, Jr. et al., "Practical Considerations in the Production, Purification, and Formulation of Monoclonal Antibodies for Immunoscintigraphy and Immunotherapy," *Seminars in Nuclear Medicine*, XIX(3):202-220 (1989).

Bonin-Debs et al., "Development of secreted proteins as biotherapeutic agents," *Expert Opin. Biol. Ther.*, 4(4):551-558 (Apr. 4, 2004).

Bonini-Filho et al., "Intravitreal Injection Versus Sub-Tenon's Infusion of Triamcinolone Acetonide for Refractory Diabetic Macular Edema: A Randomized Clinical Trial," *Invest. Ophthalmol. Vis. Sci.*, 46(10):3845-3849 (Oct. 2005).

Bontempo, "Preformulation Development of Parenteral Biopharmaceuticals," in *Drugs and the Pharmaceuticals Sciences: Development of Biopharmaceutical Parenteral Dosage Forms*, vol. 85, Bontempo (ed.), Marcel Dekker, Inc., New York, NY, pp. 91-142 (Jul. 24, 1997).

Bontempo, "Preformulation Development of Parenteral Biopharmaceuticals," Drugs and the Pharmaceutical Sciences, 85:91-108 (1997).

Borys et al., "Culture pH affects expression rates and glycosylation of recombinant mouse placental lactogen proteins by Chinese hamster ovary (CHO) cells," *Biotechnology*, 11, 720-724 (1993).

Brange, "Physical Stability of Proteins," in *Pharmaceutical Formulation Development of Peptides and Proteins*, Frokjaer, S. and Hovgaard, L. (eds.), London: Taylor & Francis, pp. 89-112 (eBook published Dec. 15, 1999).

Byrn et al., "Biological properties of a CD4 immunoadhesin," *Nature*, 344:667-670 (1990).

Cantrill et al., "Treatment of Cytomegalovirus Retinitis with Intravitreal Ganciclovir: Long-term Results," *Ophthalmology*, 96(3):367-374 (Mar. 1989).

Capon et al., "Designing CD4 immunoadhesins for AIDS therapy," *Nature*, 337:525-531 (1989).

Carpenter et al., "Rational design of stable lyophilized protein formulations: some practical advice," *Pharm. Res.*, 14(8):969-975 (1997).

Center for Drug Evaluation and Research, Application No. 21-756, Approved Labeling for Macugen® (pegaptanib sodium injection), 10 pp. (Dec. 17, 2004).

Center for Drug Evaluation and Research, Application No. 21-756, Medical Review(s), Macugen®, 98 pp. (2004).

Center for Drug Evaluation and Research, Approval Package for Application No. STN/BLA 125075/0, approved labeling for Raptiva (efalizumab) for Injection, subcutaneous, 34 pp. (Oct. 24, 2003).

Center for Drug Evaluation and Research, Approval Package for: Application No. 21-756, Macugen (pegaptanib sodium injection, 0.3 mg), 8 pp. (approval date Dec. 17, 2004).

Certificate of Correction dated Mar. 3, 2020, in U.S. Pat. No. 10,464,992, 1 pg.

Chan et al., "Evaluation of a luminescent ruthenium complex immobilized inside Nafion as optical pH sensor," *Analyst*, 123:1843-1847 (1998).

Chang et al., "Long-Term Stability of Anti-Vascular Endothelial Growth Factor (a-VEGF) Biologics Under Physiologically Relevant Conditions and Its Impact on the Development of Long-Acting Delivery Systems," *J. Pharm. Sci.*, 110(2):860-870 (available online Oct. 4, 2020).

Chang et al., "Mechanism of Protein Stabilization by Sugars During Freeze-Drying and Storage: Native Structure Preservation, Specific Interaction, and/or Immobilization in a Glassy Matrix?," *J. Pharm. Sci.*, 94(7):1427-1444 (Jul. 2005).

Chang et al., "Practical Approaches to Protein Formulation Development," in *Rational Design of Stable Protein Formulations— Theory and Practice* (J.F. Carpenter and M.C. Manning eds.), Kluwer Academic/Plenum pubs. (NY), pp. 1-25 (2002).

Charman et al., "Techniques for Assessing the Effects of Pharmaceutical Excipients on the Aggregation of Porcine Growth Hormone," *Pharmaceutical Research*, 10(7):954-962 (Jul. 1993).

Cheng et al., "On Calibration of pH Meters," *Sensors*, 5:209-219 (Apr. 27, 2005).

Chi et al., "Physical Stability of Proteins in Aqueous Solution: Mechanism and Driving Forces in Nonnative Protein Aggregation," *Pharmaceutical Research*, 20(9):1325-1336 (2003).

Chirila et al., "The Vitreous Humor," in *Handbook of Biomaterial Properties*, Black et al. (eds.), Chapman & Hall, London, England, pp. 125-126 (1998).

Chou et al., "Effects of Tween 20® and Tween 80® on the Stability of Albutropin During Agitation," *Journal of Pharmaceutical Sciences*, 94(6):1368-1381 (2005).

Christensen, "Proteins as Buffers," Annals New York Academy of Sciences, 133(1):34-40 (1966).

Cleland et al., "Formulation and Delivery of Proteins and Peptides," *American Chemical Society*, pp. 1-19 (1994).

Cleland et al., "The Development of Stable Protein Formulations: A Close Look at Protein Aggregation, Deamidation, and Oxidation," *Critical Reviews in Therapeutic Drug Carrier Systems*, 10(4):307-377 (1993).

Clinicaltrials.gov, NCT00056836, "A Study to Evaluate rhuFab V2 in Subjects With Minimally Classic or Occult Subfoveal Neovascular Macular Degeneration," online archive of <https://classic.clinicaltrials.gov/ct2/history/NCT00056836?A=2&B=2&C=merged#StudyPageTop >, Version 2, 3 pp. (Mar. 25, 2003).

Clinicaltrials.gov, NCT00061594, "A study to compare rhuFab V2 with verteporfin photodynamic in Treating Subfoveal Neovascular Macular Degeneration," online archive of <https://classic.clinicaltrials.gov/ct2/history/NCT00061594?A=2&B=2&C=merged#StudyPageTop>, Version 2, 7 pp. (Mar. 25, 2003).

Clinicaltrials.gov, NCT00090623, "A study to compare rhuFab V2 (Ranibizumab) in subjects with subfoveal choroidal Neovascularization secondary to age-related Macular Degeneration (AMD)," online archive of <https://classic.clinicaltrials.gov/ct2/history/NCT00090623?A=1&B=1&C=merged#StudyPageTop>, Version 1, 3 pp. (Jun. 23, 2005).

Clinicaltrials.gov, NCT00095433, "Extension study of rhuFab V2 in subjects with neovascular age-related macular degeneration (AMD)," online archive of <https://classic.clinicaltrials.gov/ct2/history/NCT00095433?A=1&B-1&C=merged#StudyPageTop>, Version 1, 3 pp. (Jun. 23, 2005).

Controls in SCI experiments, RegenBase, retrieved January 6, 2021, from <http://regenbase.org/control-groups.html>, as submitted to the USPTO on Jan. 7, 2021, in Inter Partes Review No. IPR2021-00402, 2 pp.

Cordeiro et al., Abstract, "Intravitreal Bevacizumab for Macular Edema Associated with Hemiretinal and Central Retinal Vein Occlusion," *Investigative Ophthalmology & Visual Science*, vol. 47(13):4257, ARVO Annual Meeting Abstract (May 2006).

Cold Spring Harbor Symposia on Quantitative Biology, vol. LXX, "Molecular Approaches to Controlling Cancer," available at www.cshl-symposium.org, 31 pp., Cold Spring Harbor Press (2005).

(56) References Cited

OTHER PUBLICATIONS

Costa et al., "Intravitreal Bevacizumab for Choroidal Neovascularization Caused by AMD (IBeNA Study): Results of a Phase 1 Dose-Escalation Study," *Invest. Ophthalmol. Vis. Sci.*, 47(10):4569-4578 (Oct. 2006).

Creighton, ed., "1.3.6 The Amide Residues: Asn and Gln," in *Proteins, Structures and Molecular Properties*, 2nd ed., WH Freeman & Company, New York, p. 9 (Aug. 15, 1992).

Crommelin et al., "Delivery of Pharmaceutical Proteins," in *Pharmaceuticals, The Science of Dosage Form Design*, 2nd ed., Aulton et al., (eds.), Churchill Livingstone, Edinburgh, UK, Chapter 35, pp. 544-553 (Jan. 2002).

Crowley, "Solutions, Emulsions, Suspensions, and Extracts," in *Remington: The Science and Practice of Pharmacy*, Martin, EW (ed.) (21st ed.), Ch. 39, pp. 745-775 (Lippincott Williams & Wilkins) (May 15, 2005).

Cunningham et al., "A Phase II Randomized Double-Masked Trial of Pegaptanib, an Anti-Vascular Endothelial Growth Factor Aptamer, for Diabetic Macular Edema," *Ophthalmology*, 112(10):1747-1757 (Published online Sep. 9, 2005).

Danis et al., "Intravitreal Triamcinolone Acetonide in Exudative Age-Related Macular Degeneration," *Retina*, 20(3):244-250 (Mar. 2000).

Daugherty et al., "Formulation and delivery issues for monoclonal antibody therapeutics," *Adv. Drug Delivery Rev.*, 58(506):686-706 (2006).

Decision on Petition Under 37 CFR 1.181 mailed Sep. 30, 2021, in Reexam Control No. 90/014,448 (10 pp.).

Declaration in Support of Request for Ex Parte Reexamination of U.S. Pat. No. 10,406,226 (Dix et al.) by Steven M. Chamow, Ph.D. executed Feb. 5, 2020.

Declaration of Dr. Laird Forrest, dated Nov. 27, 2024, 90 pp., submitted as Exhibit 1002 in IPR 2025-00233.

Declaration of Dr. Ralph Tarantino in Support of Petition for Post Grant Review of U.S. Pat. No. 10,857,231, executed Sep. 7, 2021 (236 pp.).

Declaration of Dr. Reiner Gentz, as submitted to the USPTO on Jan. 7, 2021, in Inter Partes Review No. IPR2021-00402, 76 pp.

Declaration of Dr. Todd Lefkowitz dated Nov. 29, 2024, 26 pp., submitted as Exhibit 1005 in IPR 2025-00233.

Declaration of Dr. Zhaohui Sunny Zhou, dated Nov. 29, 2024, 25 pp., submitted as Exhibit 1007 in IPR 2025-00233.

Declaration of Prof. Clive Wilson, filed in Opposition to European Patent No. 2 944 306 B1, executed Oct. 26, 2021 (75 pp.).

Declaration of Rachel J. Watters, submitted in Petition for Post Grant Review of U.S. Pat. No. 10,857,231, executed Sep. 3, 2021 (21 pp.).

Declaration Pursuant to 37 C.F.R. § 1.131 of Daniel B. Dix, Kelly Frye, and Susan Kautz in Support of Response to Office Action in U.S. Appl. No. 12/835,065, filed Nov. 22, 2011, as submitted to the USPTO on Jan. 7, 2021, in Inter Partes Review No. IPR2021-00402, 11 pp.

Demircan et al., "Determination of vitreous interleukin-1 (IL-1) and tumour necrosis factor (TNF) levels in proliferative diabetic retinopathy," *Eye*, 20:1366-1369 (Nov. 11, 2005).

*Development and Manufacture of Protein Pharmaceuticals*, Steven L. Nail and Michael J. Akers (eds.), Pharmaceutical Biotechnology, vol. 14, DOI 10.1007/978-1-4615-0549-5, © Springer Science+Business Media New York (2002).

Diehl et al., "A Good Practice Guide to the Administration of Substances and Removal of Blood, Including Routes and Volumes," *Journal of Applied Toxicology*, 21:15-23 (2001).

Ding et al., "Cellular Reparative Mechanisms of Mesenchymal Stem Cells for Retinal Diseases," *International Journal of Molecular Sciences*. 18(8):1406 (Jul. 28, 2017).

Disclaimer In Patent Under 37 C.F.R. § 1.321(a) of Frank R. Cottingham, Ph.D., J.D., in U.S. Pat. No. 10,857,231, executed Mar. 14, 2022 (1 pg.).

Drickamer et al., "Evolving views of protein glycosylation," *TIBS*, 23:321-324 (Sep. 1, 1998).

Drug Approval Package: Avastin (Bevacizumab) NDA #125085, 2 pp. (2005).

Drug Approval Package: Lucentis (Ranibizumab) Injection Company: Genentech, Inc. Application No. 12156, 2 pgs (2006).

Drug Approval Package: Macugen (Pegaptanib Sodium) Injection Company: Eyetech Pharmaceuticals, Inc. Application No. 021756, 2 pp. (2005).

Drug Vehicle (Code C927), National Cancer Institute (NCI), retrieved Jan. 6, 2021, from <https://ncithesaurus.nci.nih.gov/ncitbrowser/ConceptReport jsp?dictionary=NCI_Thesaurus&ns=ncit&code=C927 >, as submitted to the USPTO on Jan. 7, 2021, in Inter Partes Review No. IPR2021-00402 as Exhibit 1033 (2 pp.).

Drugs.com, "Lucentis: Genentech Submits Biologics License Application for FDA Review of Lucentis in Wet Age-Related Macular Degeneration," https://www.drugs.com/nda/lucentis_051230.html (Dec. 30, 2005).

Dunleavy, "Special Reports: Humira," Fiercepharma (May 3, 2021) <https://www.fiercepharma.com/special-report/top-20-drugs-by2020-sales-humira> (Accessed on Nov. 19, 2021).

Duvvuri et al., "Drug Delivery to the Retina: Challenges and Opportunities," *Expert Opinion on Biological Therapy*, 3(1):45-56 (2003).

Dwek, "Glycobiology: Toward Understanding the Function of Sugars," *Chem. Rev.*, 96(2):683-720 (Mar. 28, 1996).

Economides et al., "Cytokine traps: multi-component, high-affinity blockers of cytokine action," *Nature Medicine*, 9(1):47-52 (Dec. 16, 2002).

Edelman et al., "The Covalent Structure of an Entire γG Immunoglobulin Molecule," *Proc. Natl. Acad. Sci. USA*, 63(1):78-85 (May 15, 1969).

Eldeeb et al., "One-year outcomes of ziv-aflibercept for macular edema in central retinal vein occlusion," *American Journal of Ophthalmology Case Reports*, 8:58-61 (Available online Oct. 6, 2017).

Ellison et al., "The nucleotide sequence of a human immunoglobin C. Gene," *Nucleic Acids Research*, 10(13):4071-4079 (Jul. 10, 1982).

ENBREL® Label (Revised Jul. 2005) (64 pp.).

EPOGEN® Prescribing Information (Revised Sep. 2017) (59 pp.).

European Medicines Agency, European Public Assessment Report, Scientific Discussion—Lucentis, 54 pp. (2007).

European Pharmacopoeia, 5th ed, 4.1.3 Buffer solutions 430-435 (Jan. 1, 2005).

European Search Report dated Aug. 12, 2015, in EP Application 15169936.

European Search Report dated Aug. 4, 2011, in EP Application 11157965.

European Search Report dated Feb. 28, 2013, in EP Application 13152402.

European Search Report dated Nov. 12, 2020, in EP Application 20178021.

Ex Parte Request for Reexamination of U.S. Pat. No. 10,464,992, pp. 1-70, published Feb. 11, 2020.

Excerpts from Antibody Fusion Proteins (S.M. Chamow & A. Ashkenazi (eds.) 221-309 (1999).

Expert Declaration of Dr. Peter Tessier in Support of Petition for Inter Partes Review of U.S. Pat. No. 10,406,226, dated Feb. 23, 2023, in IPR2023-00620 (60 pp.).

Expert Declaration of Dr. Ralph Tarantino in Support of Petition for Inter Partes Review of U.S. Pat. No. 10,464,992, filed Jan. 17, 2023, in IPR2023-00462 (85 pp.).

Expert Declaration of Richard Manning, Ph.D., submitted in IPR2021-00881 (U.S. Pat. No. 9,254,338), 289 pp., dated Feb. 11, 2022.

Eylea SmPC Summary of Product Characteristics, in German (5 pp.) with English machine translation (5 pp.), submitted in German revocation proceeding on May 24, 2023.

EYLEA® Highlights of Prescribing Information, 15 pp. (rev. Nov. 2011).

EYLEA® Product Insert (Revised Feb. 2023) (38 pp.).

EYLEA® Product Insert (Revised Mar. 2021) (32 pp.).

EYLEA® Product Insert (Revised Jul. 2021) (36 pp.).

(56) References Cited

OTHER PUBLICATIONS

Fahrer et al., "Industrial Purification of Pharmaceutical Antibodies: Development, Operation, and Validation of Chromatography Processes," *Biotechnology and Genetic Engineering Reviews*, 18(1):pp. 301-327 (Jul. 2001).
Falconer, "Advances in Liquid Formulations of Parenteral Therapeutic Proteins," *Biotechnology Advances*, 37(7):107412, 9 pp. (Jun. 27, 2019).
Fasman, ed., "Buffer Solutions," in *Practical Handbook of Biochemistry and Molecular Biology*, CRC Press LLC, Boca Raton, FL, pp. 544-546 and 555-557 (1992).
Fast et al., "Physical Instability of a Therapeutic Fc Fusion Protein: Domain Contributions to Conformational and Colloidal Stability," *Biochemistry*, 48(49):11724-11736 (2009).
FDA, "Pharmaceutical Excipient Evaluation Guidelines," the Ministry of Food and Drug Safety (MFDS) of South Korea guidelines for drug additives (May 2007) (46 pp. in Korean, with 46 pp. machine translation to English).
Ferrara et al., "Development of Ranibizumab, an Anti-Vascular Endothelial Growth Factor Antigen Binding Fragment, as Therapy for Neovascular Age-Related Macular Degeneration," *Retina*, 26:859-870 (2006).
Ferrara et al., "Angiogenesis as a therapeutic target," *Nature*, 438:967-974 (Dec. 2005).
Ferrara et al., "Bevacizumab (Avastin), A Humanized Anti-VEGF Monoclonal Antibody For Cancer Therapy," *Biochem. Biophys. Res. Commun.*, 333(2):328-335 (available online Jun. 2, 2005).
Ferrara et al., "Vascular Endothelial Growth Factor: Basic Science and Clinical Progress," *Endocr. Rev.*, 25(4):581-611 (Aug. 1, 2004).
File History of U.S. Appl. No. 16/535,610, filed Aug. 8, 2019, which issued as U.S. Pat. No. 10,857,231 on Dec. 8, 2020 (283 pp.).
File History of U.S. Pat. No. 10,464,992, as submitted to the USPTO on Jan. 7, 2021, in Inter Partes Review No. IPR2021-00402, 124 pp.
Fransson et al., "Local Tolerance of Subcutaneous Injections," *J. Pharm. Pharmacol.*, 48:1012-1015 (1996).
Fraser et al., "Single Injections of Vascular Endothelial Growth Factor Trap Block Ovulation in the Macaque and Produced Prolonged, Dose-Related Suppression of Ovarian Function," *J. Clin. Endocrin. & Metabol.*, 90(2):1114-1122 (Feb. 2005).
Frenken et al., "Identification of the Component Part in an Epoctin Alfa Preparation That Causes Pain After Subcutaneous Injection," *American Journal of Kidney Diseases*, 22(4):553-556 (1993).
Frokjaer et al., "Pharmaceutical Formulation Development of Peptides and Proteins," Taylor & Francis, Philadelphia, PA, pp. 146-171 (2000).
Funatsu et al., "Increased levels of vascular endothelial growth factor and interleukin-6 in the aqueous humor of diabetics with macular edema," *Am. J. Ophthalmol.*, 133:70-77 (Available online Dec. 21, 2001).
Gallemore et al., "Intravitreal Kenalog Injections," *EyeNet Magazine*, 5 pp., available online at https://www.aao.org/eyenet/article/intravitreal-kenalog-injections (published online Oct. 1, 2004).
Gandorfer et al., "Posterior Vitreous Detachment Induced by Microplasmin," *Invest. Ophthalmol. Vis. Sci.*, 45(2):641-647 (Feb. 2004).
Garcia-Carmona et al., "Morphological characteristics and aggregation of calcite crystals obtained by bubbling $CO_2$ through a $Ca(OH)_2$ suspension in the presence of additives," *Powder Technology*, 130(1-3):307-315 (Feb. 19, 2003).
Garcia-Valldecabres et al., "pH Stability of ophthalmic solutions," *Optometry*, 75(3):161-168 (Mar. 2004).
Gasteiger et al., "ExPASy: the proteomics server for in-depth protein knowledge and analysis," *Nucleic Acids Research*, 31(13):3784-3788 (2003).
Gaudreault et al., "Preclinical Pharmacokinetics of Ranibizumab (rhuFabV2) After a Single Intravitreal Administration," *Investigative Ophthalmology & Visual Science*, 46(2):726-733 (Feb. 2005).
Genentech Drug Notification regarding Avastin, 2 pp., dated Dec. 19, 2008.
Genentech Warning letter regarding Avastin, 2 pp., dated Aug. 28, 2006.
Gerber et al., "Complete Inhibition of Rhabdomyosarcoma Xenograft Growth and Neovascularization Requires Blockage of Both Tumor and Host Vascular Endothelial Growth Factor," *Cancer Res.*, 60:6253-6258 (Nov. 15, 2000).
Chate et al., "Ocular Drug Delivery," *Expert Opinion on Biological Therapy*, 3(2):275-287 (2006).
Gierasch, "Signal Sequences," *Biochemistry*, 28(3):923-930 (Feb. 7, 1989).
Gillies et al., "A Randomized Clinical Trial of a Single Dose of Intravitreal Triamcinolone Acetonide for Neovascular Age-Related Macular Degeneration," *Arch. Ophthalmol.*, 121(5):667-673 (May 2003).
Gjølberg et al., "A silicone oil-free syringe tailored for intravitreal injection of biologics," *Frontiers in Ophthalmology*, vol. 2, Art. 882013 (May 3, 2022).
Glade-Blender et al., "VEGF Blocking Therapy in the Treatment of Cancer," *Expert Opinion on Biological Therapy*, Ashley London GB 3(2):263-276 (Apr. 2003).
Gokarn et al., "Excipients for Protein Drugs," *Excipient Development for Pharmaceutical, Biotechnology, and Drug Delivery Systems*, 291-331 (2006).
GONAL-F® Prescribing Information (Revised Dec. 2020) (33 pp.).
Gragoudas et al., "Pegaptanib for Neovascular Age-Related Macular Degeneration," The New England Journal of Medicine, 2004; 351(27):2805-16 (Dec. 30, 2004).
Gragoudas et al., "Pegaptanib for Neovascular Age-Related Macular Degeneration," *The New England Journal of Medicine*, Supplementary Appendix, 10 pp., 351(27) :2805-16 (Dec. 30, 2004).
Graham et al., "Intravitreal Injection of Dexamethasone—Treatment of Experimentally Induced Endophthalmitis," *Arch Ophthalmol.*, 92(2):149-154 (Aug. 1974).
Hanks Solution <http://www.lifetechnologies.com/us/en/home/technical-resources/media-formulation.152.html> (Accessed on Dec. 19, 2013).
Hanna Instruments, User's Manual, Checker®, HI 98103 pH tester with replaccable electrode, 2 pp. (Dec. 2004).
Harris, "Processing of C-terminal lysine and arginine residues of proteins isolated from mammalian cell culture," Journal of Chromatography A, 705:129-134 (1995).
Harris, "Processing of C-terminal lysine and arginine residues of proteins isolated from mammalian cell culture," *Journal of Chromatography A*, 705(1):129-134 (Jun. 23, 1995).
Hart, "Glycosylation," *Curr. Opin. Cell Biol.*, 4(6):1017-1023 (Dec. 1992).
Healio News, "VEGF Trap study for AMD Begins," 1 p., available at https://www.healio.com/news/ophthalmology/20120331/vegf-trap-study-for-amd-begins (Mar. 11, 2004).
Heier et al., "Randomized, controlled phase III study of Ranibizumab (Lucentis™) for minimally classic or occult neovascular age-related macular degeneration: two-year efficacy results of the MARINA study," ARVO Annual Meeting Abstract, *Investigative Ophthalmology & Visual Science*, vol. 47(13), 2959, 2 pp. (May 2006).
Heier et al., "RhuFab V2 in Wet AMD—6 Month continued improvement following multiple intravitreal injections," ARVO Annual Meeting Abstract, *Investigative Ophthalmology & Visual Science*, 44(13):972 (May 2003).
Heier et al., "RhuFab V2 (an anti-VEGF antibody fragment) in neovascular AMD: Safety and tolerability of multiple intravitreal injections," ARVO Annual Meeting Abstract, *Investigative Ophthalmology & Visual Science*, 43(13):2520 (Dec. 2002).
HERCEPTIN® label (Sep. 1998) (2 pp.).
HERCEPTIN®, *Physician's Desk Reference*, 59th Ed., Thompson PDR (NJ), pp. 313 & 1337-1341 (2005).
Hermosilla et al., "Comprehensive biophysical and functional study of ziv-aflibercept: characterization and forced degradation," *Scientific Reports*, 10(2675):1-13 (2020).
Heymans et al., "Risks of Intravitreal Use of Bevacizumab (Avastin®))," *Arzneimittel im Blick* (Medicinal Products at a Glance), Issue 4, pp. 3-12 (with English translation, 10 pp.) (Dec. 2012).

(56) References Cited

OTHER PUBLICATIONS

Hida et al., "Experimental and Clinical Observations of the Intraocular Toxicity of Commercial Corticosteroid Preparations," *American Journal of Ophthalmology*, 101(2):190-195 (Feb. 1986).
Highlights of Prescribing Information for Lucentis® (ranibizumab injection) for intravitreal injection, 2 pp., initial US approval: 2006, revised Feb. 2024.
Hirvonen et al., "Hydrodynamic Radii of Ranibizumab, Aflibercept and Bevacizumab Measured by Time-Resolved Phosphorescence Anisotropy," *Pharm Res*, 33:2025-2032 (2016).
Holash et al., "VEGF-Trap: A VEGF blocker with potent antitumor effects," *PNAS*, 99(17):11393-11398 (2002).
Hossler et al., "Optimal and consistent protein glycosylation in mammalian cell culture," *Glycobiology*, 19(9):936-949 (2009).
Huang et al., "Regression of established tumors and metastases by potent vascular endothelial growth factor blockade," *PNAS*, 100(13):7785-7790 (2003)
HUMALOG® Prescribing Information (Mar. 2013) (27 pp.).
HUMIRA™ Label (Dec. 20, 2002) (17 pp.).
ICH, Guidance for Industry: Q5C Quality of Biotechnological Products: Stability Testing of Biotechnological/Biological Products, 9 pp. (Jul. 1996).
ICH, Guidance for Industry: Q6B Specifications: Test Procedures and Acceptance Criteria for Biotechnological/Biological Products, 17 pp. (Sep. 1999).
Illingworth, "A common source of error in pH measurements," *Biochem. J.*, 195(1):259-262 (Apr. 1, 1981).
Imperiali et al., "Asparagine-Linked Glycosylation: Specificity and Function of Oligosaccharyl Transferase," *Bioorganic & Medicinal Chemistry*, 3(12):1565-1578 (Dec. 1995).
INFERGEN® Prescribing Information (Revised Jul. 2010) (39 pp.).
International Preliminary Report on Patentability dated Sep. 25, 2007, for International Application PCT/US2006/010600.
International Search Report dated Sep. 19, 2006, for International Appln. PCT/US2006/010600.
International Search Report, mailed Apr. 3, 2008, in International Appln. PCT/US2007/014085.
Intravitreal VEGF Trap looking promising, p. 1 (Feb. 21, 2006) <https://europe.ophthalmologytimes.com/view/intravitreal-vegf-trap-looking-promising>.
INTRON® A Prescribing Information (Revised Nov. 1997) (37 pp.).
Ionescu et al., "Contribution of Variable Domains to the Stability of Humanized IgG1 Monoclonal Antibodies," *J. Pharm. Sci.*, 97(4):1414-1426 (Apr. 2008).
IPR2023-00462, Paper 2, Petition for Inter Partes Review of U.S. Pat. No. 10,464,992 (77 pp.) (Jan. 17, 2023).
IPR2023-00620, Paper 2, Petition for Inter Partes Review of U.S. Pat. No. 10,406,226 (75 pp.) (dated Feb. 28, 2023).
Iturralde et al., "Intravitreal bevacizumab (Avastin) treatment of macular edema in central retinal vein occlusion: a short-term study," *Retina*, 26(3):279-284 (Mar. 26, 2006).
Jacob et al., "Stability of Proteins in Aqueous Solution and Solid State," *Indian J of Pharm Sci*, 68(2):154-163 (Mar.-Apr. 2006).
Jaffe et al. (eds.), Intraocular Drug Delivery, Taylor & Francis Group, New York, NY, 370 pp. (ebook published Mar. 12, 2006).
Jager et al., "Risks of Intravitreous Injection: A Comprehensive Review," *Retina*, 24(5):676-698 (Oct. 2004).
Jaissle et al., "Intravitreal injections—High Standards of Procedure Necessary," *Klin Monatsbl Augenheilkd*, 222:389, 4 pp. (2005) (with English language translation).
Janeway et al., "The structure of a typical antibody molecule," *Immunobiology: The Immune System in Health and Disease*, 5th edition, New York: Garland Science, 6 pp. (2001).
Jefferis, "Glycosylation as a strategy to improve antibody-based therapeutics," *Nat. Rev. Drug Discov.*, 8(3):226-34 (Mar. 2009).
Jefferis, "Glycosylation of Recombinant Antibody Therapeutics," Biotechnol. Prog., 21:11-16 (2005).
Jonas et al., "Intraocular pressure after intravitreal injection of triamcinolone acetonide," *Br. J. Ophthalmol.*, 87:24-27 (Jan. 2003).
Jonas et al., "Intravitreal triamcinolone acetonide for treatment of intraocular proliferative, exudative, and neovascular diseases," *Progress in Retinal and Eye Research*, 24(5):587-611 (Sep. 2005).
Kalantar-Zadeh, "History of Erythropoiesis-Stimulating Agents, the Development of Biosimilars, and the Future of Anemia Treatment in Nephrology," American Journal of Nephrology, 45:235-247 (2017).
Katayama et al., "Retrospective statistical analysis of lyophilized protein formulations of progenipoietin using PLS: determination of the critical parameters for long-term storage stability," *J. Pharm. Sci.*, 93(10):2609-2623 (2004).
Kenalog®-40 Injection (triamcinolone acetonide injectable suspension, USP) label, 20 pp. (November 20, 2006).
Kendall et al., "Inhibition of Vascular Endothelial cell growth factor Activity by an Endogenously encoded soluble receptor," *Proc. Natl. Acad. Sci. USA*, 90:10705-10709 (Nov. 15, 1993).
Kendrick et al., "Physical Stability of Proteins in Aqueous Solution,," in *Rational Design of Stable Protein Formulations*, pp. 61-84, Kluwer Academic/Plenum publishers, New York, NY(2002).
Kerwin, "Polysorbates 20 and 80 Used in the Formulation of Protein Biotherapeutics: Structure and Degradation Pathways," Journal of Pharmaceutical Sciences, 97(8):2924-2935 (2008).
Kim et al., "Antibody Engineering for the Development of Therapeutic Antibodies," *Mol. Cells*, 20(1):17-29 (Aug. 31, 2005).
Kim et al., "Effect of Intravitreal Injection of Ranibizumab in Combination with Verteporfin PDT on Normal Primate Retina and Choroid," *Investigative Ophthalmology & Visual Science*, 47(1):357-363 (Jan. 2006).
Kim et al., "Potent VEGF blockade causes regression of coopted vessels in a model of neuroblastoma," *PNAS*, 99(17):11399-11404 (2002).
Kimura et al., "Glycosylation of CHO-Derived Recombinant tPA Produced under Elevated pCO2," *Biotechnol. Prog.*, 13(3):311-317 (May-Jun. 1997).
KINERET® Prescribing Information (Revised Dec. 2020) (18 pp.).
Kobata, "A journey to the world of glycobiology," *Glycoconjugate Journal*, 17:443-464 (Jul. 2000).
Kompa et al., "Corneal calcification after chemical eye burns caused by eye drops containing phosphate buffer," *Burns*, 32(6):744-747 (Jul. 10, 2006).
Kostanski et al., "Size-exclusion chromatography—a review of calibration methodologies," *J. Biochem. Biophys. Methods*, 58:159-186 (2004).
Krapp et al., "Structural Analysis of Human IgG-Fc Glycoforms Reveals a Correlation Between Glycosylation and Structural Integrity," *Journal of Molecular Biology*, 325(5):pp. 979-989 (2003).
Krishnan et al., "Development of Formulations for Therapeutic Monoclonal Antibodies and Fc Fusion Proteins," in *Formulation and Process Development Strategies for Manufacturing Biopharmaceuticals*, pp. 383-427, John Wiley & Sons, Inc., New Jersey, NY (2010).
Krzystolik et al., "Prevention of experimental choroidal neovascularization with intravitreal anti-vascular endothelial growth factor antibody fragment," *Arch Ophthalmol*, 120(3):338-346 (Mar. 2002).
Kuppermann et al., "Pooled Efficacy Results From Two Multinational Randomized Controlled Clinical Trials of a Single Intravitreous Injection of Highly Purified Ovine Hyaluronidase (Vitrase®) for the Management of Vitreous Hemorrhage," *Am. J. Ophthalmol.*, 140(4):573-584 (Aug. 26, 2005).
Kuppermann et al., "Safety Results of Two Phase III Trials of an Intravitreous injection of Highly Purified Ovine Hyaluronidase (Vitrase®) for the Management of Vitreous Hemorrhage," *Am. J. Ophthalmol.*, 140(4):585-597 (pp. 585.e1-585.e15 (Aug. 22, 2005)).
Kurnik et al., "Buffer exchange using size exclusion chromatography, countercurrent dialysis, and tangential flow filtration: Models, Development, and Industrial Application," *Biotech. and Bioeng.*, 45(2):149-157 (Jan. 20, 1995).
Lang et al., "Ophthalmic Preparations," in *Remington: The Science and Practice of Pharmacy*, (21st ed), Martin, EW (ed), Ch. 43, pp. 850-870 (Lippincott Williams & Wilkins) (May 15, 2005).
Larson et al., "The Structure of an Antitumor Ch2-domain-deleted Humanized Antibody," *J. Mol. Biol.*, 348(5):1177-1190 (Apr. 1, 2005).

(56) References Cited

OTHER PUBLICATIONS

Laursen et al., "Pain Perception after Subcutaneous Injections of Media Containing Different Buffers," *Basic & Clinical Pharmacology & Toxicology*, 98:218-221 (Jan. 2006).
Lehninger, "27.3 Protein Targeting and Degradation," in *Principles of Biochemistry*, 4th ed., Nelson et al. (eds.), Chapter 27, pp. 1068-1070 (Apr. 23, 2004).
Lesslauer, "TNF Receptor IgG Fusion Protein: Principles, Design, and Activities," in *Antibody Fusion Proteins* (Chamow et al., eds.), Wiley Liss (a John Wiley & Sons Inc. publication), New York, NY, Chapter 9, pp. 243-279 (Apr. 13, 1999).
Liu et al., "Antibody drug product information: current status and future directions," Regeneron Presentation, Eighth Annual The Bioprocessing Summit, Boston, Massachusetts, 28 pp. (Aug. 15-19, 2016).
Liu, "Antibody Glycosylation and Its Impact on the Pharmacokinetics and Pharmacodynamics of Monoclonal Antibodies and Fc-Fusion Proteins," *J. Pharm. Sci.*, 104(6):1866-1884 (Jun. 2015).
Liu, "Antibody Glycosylation and Its Impact on the Pharmacokinetics and Pharmacodynamics of Monoclonal Antibodies and Fc-Fusion Proteins," *Journal of Pharmaceutical Sciences*, 104:pp. 1866-1884 (Apr. 14, 2015).
Lodish et al., "17.4 Der Transport von Sekretproteinen durch die Membran des ER," in *Molekulare Zellbiologie* (4th ed.), Spektrum Akademischer Verlag Heidelberg Berlin, pp. 754-757 and 771-773 (2001), with machine translation.
Lodish et al., "Synthesis and assembly of membrane and organelle proteins," *Int. Rev. Cytol. Suppl.*, 12, pp. 247-307 (1981).
Lopez et al., "Comparative enhancer effects of Span 20 with Tween 20 and Azone of the in vitro percutaneous penetration of compounds with different lipophilicites" *International Journal of Pharmaceutics*, 202(1-2):133-140 (2000).
LUCENTIS® Approval Letter, Center for Drug Evaluation and Research Approval Package for Application No. 125156, 29 pp. (Jun. 2006).
LUCENTIS® label (2006) (2 pp.).
LUCENTIS® (ranibizumab injection), Highlights of Prescribing Information, BLA 125156/105, 14 pp. (revised Oct. 2014).
LUCENTIS®, Highlights of Prescribing Information, 7 pp. (2006).
Macugen® (Pegaptanib Sodium) Injection Drug Approval Package, FDA database, NDA #021756, 2 pp. (created Mar. 23, 2005).
Macugen® (Pegaptanib Sodium) Injection, FDA Drug Approval Package, FDA Center for Drug Evaluation and Research, NDA 21-756, 2 pp. (approval date Dec. 17, 2004).
MACUGEN® Approval Package, Center for Drug Evaluation and Research, Application No. 21-756, 8 pp. (Dec. 17, 2004).
MACUGEN® Approved label, Center for Drug Evaluation and Research, Application No. 21-756, pp. 4-11 (Dec. 17, 2004), 10 pp.
Macugen® Approved Label, FDA Drug approval package, NDA 21-756, pp. 4- 11 (2005).
Macugen® Label, NDA 21-756, pp. 4-11 (revised Jul. 2011).
Macugen® Label, NDA 21-756/S-006 and NDA 21-756/S-007, pp. 3-10 (Mar. 8, 2006).
MACUGEN® Product Label dated Sep. 17, 2004.
MACUGEN® Product Monograph dated Apr. 25, 2005.
Malik et al., "Safety profiles of anti-VEGF drugs: bevacizumab, ranibizumab, aflibercept and ziv-aflibercept on human retinal pigment epithelium cells in culture," *Br. J. Ophthalmol.*, 98:i11-i16 (May 17, 2014).
Malingre et al., "The Co-Solvent Cremophor EL Limits Absorption of Orally Administered Paclitaxel in Cancer Patients," *British Journal of Cancer*, 85(10):1472-1477 (2001).
Manzano et al., "Testing Intravitreal Toxicity of Bevacizumab (Avastin)," *Retina*, 26(3):257-261 (2006).
Marinaro et al., "O-glycosylation delays the clearance of human IGF-binding protein-6 from the circulation," *European Journal of Endocrinology*, 142(5):512-516 (May 1, 2000).
Marmor et al., "Osmotically induced retinal detachment in the rabbit and primate: electron microscopy of the pigment epithelium," *Inv. Ophth & Vis. Sci.*, 19(9):1016-1029 (Sep. 1980).
Marra et al., "Solution Formulation Development of a VEGF Inhibitor for Intravitreal Injection," *AAPS PharmSciTech*, 12(1):362-371 (Mar. 2011).
McGoff et al., "Solution Formulation of Proteins/Peptides," in *Drugs and the Pharmaceutical Sciences*, vol. 99: Protein Formulation and Delivery (E.J. McNally ed.), Marcel Dekker, Inc. pub. (NY), pp. 139-158 (2000).
Meyer et al., "Effects of Conformation on the Chemical Stability of Pharmaceutically Relevant Polypeptides," in *Rational Design of Stable Protein Formulations*, Carpenter, J.F. et al. (eds.), New York: Kluwer Academic/Plenum Publishers, pp. 85-107 (Apr. 30, 2002).
Mi et al., "Effects of polyethylene glycol molecular weight and concentration on lactate dehydrogenase activity in solution and after freeze-thawing," *PDA J. Pharm. Sci. Technol.*, 56:115-123 (2002).
Michels et al., "Ranibizumab Therapy for Neovascular Age-Related Macular Degeneration," *Retinal Physician*, 1(1):16-22 (Aug. 1, 2004).
Michels et al., "Systemic Bevacizumab (Avastin) Therapy For Neovascular Age-Related Macular Degeneration Twelve-Week Results Of An Uncontrolled Open-Label Clinical Study," *Ophthalmol . . .* 112(6):1035-1047 (Jun. 2005).
Middleton et al., "Bevacizumab (Avastin®)," *Clinical Journal of Oncology Nursing*, 8(6):S.666 (Dec. 2004).
Miller et al., "Randomized, Controlled Phase III Study of Ranibizumab (Lucentis) for Minimally Classic or Occult Neovascular Age-Related Macular Degeneration: Two-ear safety Results of the MARINA Study," ARVO Annual Meeting Abstract, *Investigative Ophthalmology & Visual Science*, 47(13):3539 (May 2006).
Mimura et al., "The role of oligosaccharide residues of IgG1-Fc in FcγIIb binding," *Journal of Biological Chemistry*, 276(49):45539-45547 (Sep. 20, 2001).
Molecular Approaches to Controlling Cancer, Cold Spring Harbor Symposia on Quantitative Biology, vol. LXX, pp. xxvii-xxix (2005).
Mordenti et al., "Comparisons of the Intraocular Tissue Distribution, Pharmacokinetics, and Safety of I-Labeled Full-Length and Fab Antibodies in Rhesus Monkeys Following Intravitreal Administration," *Toxicologic Pathology*, 27(5):536-544 (Sep.-Oct. 1999).
Moreno et al., "Study of Stability and Biophysical Characterization of Ranibizumab and Aflibercept," *European Journal of Pharmaceutics and Biopharmaceutics*, 108:156-167 (Epub Sep. 8, 2016).
Moroney et al., "Aflibercept in epithelial ovarian carcinoma," *Future Oncol.*, 5(5):591-600 (2009).
Mulay et al., "Safety and pharmacokinetics of intravenous VEGF Trap plus FOLFOX4 in a combination phase I clinical trial of patients with advanced solid tumors," Meeting Abstract: 2006 ASCO Annual Meeting, Journal of Clinical Oncology, 24:18 (Jun. 20, 2006).
Nayar et al., "High Throughput Formulation: Strategies for Rapid Development of Stable Protein Products, In Strategies for Rapid Development of Stable Protein Products," in Formulations, New York: Kluwer Academic/Plenum Publishers, pp. 177-198 (2002).
Ng et al., "Pegaptanib, a targeted anti-VEGF aptamer for ocular vascular disease," *Nature Reviews*, 5:123-132 (Feb. 2006).
Ng et al., "Targeting angiogenesis, the underlying disorder in neovascular age-related macular degeneration," *Can J Ophthalmol*, 4(3):352-368 (2005).
Nguyen et al., "Results of a Phase I, Dose-Escalation, Safety, Tolerability, and Bioactivity Study of Intravitreous VEGF Trap in Patients with Neovascular Age-Related Macular Degeneration," ARVO Annual Meeting Abstract, 2 pp., *Investigative Ophthalmology & Visual Science*, 47:2144 (May 2006).
Nguyen et al., "Bevacizumab Suppresses Choroidal Neovascularisation Caused By Pathological Myopia," Br. J. Ophthalmol., 89(10):1368-1370 (Sep. 16, 2005); Erratum in: *Br J Ophthalmol.* 90(1):125 (Jan. 1, 2006).
Nguyen et al., "Results of a Phase I, Dose-Escalation, Safety, Tolerability, and Bioactivity Study of Intravitreous VEGF Trap in Patients With Neovascular Age-Related Macular Degeneration," ARVO Annual Meeting Abstract, pp. 1-2 (May 2006).
Nonconfidential Brief of Appellee Regeneron Pharmaceuticals, Inc., 85 pp., filed on Aug. 26, 2024, in *Regeneron Pharmaceuticals, Inc. v. Mylan Pharmaceuticals, Inc. et al.*, in 1:24-md-3103-TSK (N.D. W.Va.).

(56) References Cited

OTHER PUBLICATIONS

NOVOLOG® Prescribing Information (Revised Feb. 2015) (51 pp.).
NUTROPIN AQ® Prescribing Information (Revised Dec. 2016) (23 pp.).
Oakton Instruments, Eutech Instruments Instruction Sheet for Waterproof pHTestr 2, Microprocessor-based Pocket pH Tester, 3 pp., Rev. 5 (Feb. 2005).
Oliveira et al., "Dispase Facilitates Posterior Vitreous Detachment During Vitrectomy in Young Pigs," *Retina*, 21(4):324-331 (Aug. 2001).
Opuviz, Summary of Product Characteristics in Dutch, 54 pp., with English machine translation (54 pp.), as submitted in related Netherlands Impeachment proceeding C/09/675574 and C/09/675547 on Feb. 5, 2025.
Opposition to Patent Owner's Petition to Vacate Ex Parte Reexamination Order or, in the Alternative, to Stay Reexamination Proceeding Pursuant To 37 C.F.R. §§ 1.181 and 1.182 in Reexam Control No. 90/014,448, executed Jun. 12, 2020 (53 pp.).
Opuviz, Summary of Product Characteristics in Dutch, 54 pp.
Order Denying Institution of Post-Grant Review Pursuant to 35 U.S.C. § 324, entered Mar. 15, 2022, in Case PGR2021-00117 (U.S. Pat. No. 10,857,231) (4 pp.).
Order Granting Request for Ex Parte Reexamination mailed Apr. 1, 2020, in Reexam Control No. 90/014,448 (21 pp.).
Order Granting Request for Ex Parte Reexamination mailed Mar. 13, 2020, in Reexam Control No. 90/014,449 (13 pp.).
Order Granting Unopposed Motions to Dismiss the Petition and Terminate the Proceeding Before Institution 37 C.F.R. §§ 42.5(a), 42.71(a) entered Jun. 25, 2021, in Inter Partes Review No. IPR2021-00402 (U.S. Pat. No. 10,464,992 B2)/PGR2021-00035 (U.S. Pat. No. 10,828,345 B2) (3 pp.).
ORENCIA® Label (Mar. 2017) (30 pp.)
Ozdemir et al., "Intravitreal triamcinolone acetonide for treatment of cystoid macular oedema in patients with retinitis pigmentosa," *Acta Ophthalmol Scand.*, 83(2):248-251 (Mar. 30, 2005).
Park, Press Release, "Nucala 40mg Prefilled Syringe Approved for Children With Severe Eosinophilic Asthma," (Jan. 25, 2022).
Parkins et al., "The formulation of biopharmaceutical products," *Pharmaceutical Science & Technology Today*, 3(4):129-137 (2000).
Patent Owner Regeneron Pharmaceuticals, Inc.'s Sur-Reply to Petitioner's Reply to Patent Owner Preliminary Response, filed Jan. 25, 2022, in Case PGR2021-00117 (U.S. Pat. No. 10,857,231) (14 pp.) (later withdrawn by the PTAB).
Patent Owner Regeneron Pharmaceuticals, Inc.'s Unopposed Motion to Withdraw Patent Owner's Preliminary Response and Surreply, filed Mar. 3, 2022, in Case PGR2021-00117 (U.S. Pat. No. 10,857,231) (4 pp.).
Patent Owner's Mandatory Notices dated Jan. 25, 2021, in Inter Partes Review No. IPR2021-00402 (7 pp.). Patent Owner's Response (redacted) from IPR2023-00462 (U.S. Pat. 10,464,992), 80 pp., dated Nov. 2, 2023.
Patro et al., "Protein Formulation and Fill-Finish Operations," *Biotechnology Annual Review*, 8:55-84 (2002).
Petition for Inter Partes Review of U.S. Pat. No. 10,464,992 Under 35 U.S.C. §§ 311-319 and 37 C.F.R. § 42.100 et seq. (Inter Partes Review No. IPR2021-00402), executed Jan. 7, 2021 (59 pp.).
Petition for Post-Grant Review of U.S. Pat. No. 10,857,231 Under 35 U.S.C. §§ 321-329 and 37 C.F.R. § 42.200 et seq. (Case PGR2021-00117), executed Sep. 7, 2021 (103 pp.).
Petition to Vacate Ex Parte Reexamination Order or, in the Alternative, to Stay Reexamination Proceeding Pursuant to 37 C.F.R. §§ 1.181 and 1.182 in Reexam Control No. 90/014,448, executed May 29, 2020 (33 pp.).
Petition to Vacate Ex Parte Reexamination Order or, in the Alternative, to Stay Reexamination Proceeding Pursuant to 37 C.F.R. §§ 1.181 and 1.182 in Reexam Control No. 90/014,449, executed May 12, 2020 (30 pp.).

Petitioner's Unopposed Motion to Terminate Proceedings Pursuant to 35 U.S.C. § 317(A) dated Jun. 23, 2021, in Inter Partes Review No. IPR2021-00402 (5 pp.).
Petitioner's Reply to Patent Owner's Preliminary Response, filed Jan. 18, 2022, in Case PGR2021-00117 (U.S. Pat. No. 10,857,231) (16 pp.).
Pfizer, "Macugen™, Pegaptanib Sodium, Antivascular Endothelium Growth Factor (VEGF185 Inhibitor) for Age-Related Macular Degeneration," in Compendium of Pharmaceuticals and Specialties: The Canadian Drug Reference for Health Professionals, Canadian Pharmacists Association, pp. 1242-1244 (2006).
Pfizer Canada Inc., Control No. 165843, Product Monograph for Macugen (pegaptanib sodium injection), pp. 1 and 15, date of preparation: Apr. 25, 2005; date of revision: Sep. 25, 2013.
Phosphate buffer, Cold Spring Harbor Protocols, 2006:pdb.rec8543, as submitted to the USPTO on Jan. 7, 2021, in Inter Partes Review No. IPR2021-00402 (1 pg.).
Poon, "Tonicity, Osmoticity, Osmolality, and Osmolarity," in *Remington: The Science and Practice of Pharmacy*, (21st ed), Martin (ed), Ch. 18, pp. 250-265 (Lippincott Williams & Wilkins) (May 15, 2005).
Powell et al., "Compendium of Excipients for Parenteral Formulations," *J. Pharm. Sci. Technol.*, 52(5):238-311 (Sep.-Oct. 1998).
Preliminary Response of Patent Owner Regeneron Pharmaceuticals, Inc. filed Apr. 14, 2021, in Case IPR2021-00402 (U.S. Pat. No. 10,464,992) (63 pp.).
Preliminary Response of Patent Owner Regeneron Pharmaceuticals, Inc. filed Dec. 15, 2021, in Case PGR2021-00117 (U.S. Pat. No. 10,857,231) (92 pp.) (later withdrawn by the PTAB).
Press Release, Novartis receives FDA approval of Xolair® (omalizumab self-injection with prefilled syringe across all indications for appropriate patients, (Apr. 12, 2021).
Press Release, Regeneron Reports Fourth Quarter and Full Year 2022 Financial and Operating Results (Feb. 3, 2023).
Rana et al., "Pharmacologic Treatment in Diabetic Macular Edema," in *Intraocular Drug Delivery*, G. Jaffe et al. (eds), Ch. 19, pp. 291-300 (Taylor & Francis) (ebook published Mar. 12, 2006).
Randolph et al., "Surfactant-Protein Interactions," *Rational Design of Stable Protein Formulations*, pp. 159-175, Springer, Boston, MA (2002).
RAPTIVA® label (Mar. 2009) (36 pp.).
RAPTIVA®, *Physician's Desk Reference*, 59th Ed., Thompson PDR (NJ), pp. 1350-1354 (2005).
*Rational Design of Stable Protein Formulations: Theory and Practice*, John F. Carpenter and Mark C. Manning (eds.), Pharmaceutical Biotechnology, vol. 13, DOI 10.1007/978-1-4615-0557-0, © Springer Science+Business Media New York (2002).
Regeneron Pharmaceuticals, "Diseases which induce vascularity in the eye cause blindness," online archive of >www.regeneron.com:80/research/disease_template.asp?v_c_id=23>, 2 pp., dated Mar. 8, 2005, accessed via the Wayback Machine.
Regeneron Pharmaceuticals, Inc. Form 8-K, United States Securities and Exchange Commission, 6 pp., report dated Feb. 1, 2006, report filed Feb. 3, 2006.
Regeneron Pharmaceuticals, Inc. Form 10-K for the year ended Dec. 31, 2004, 87 pp.
Regeneron Pharmaceuticals, Inc. Form 10-K for the year ended Dec. 31, 2005, 109 pp.
Regeneron Pharmaceuticals, Inc., Presentation, "Lehman Brothers 9th Annual Global Healthcare Conference" (March 8, 2006), available at https://web.archive.org/web/20060316092055/http:/www.regeneron.com/investor/Regn_LM_Mar06.pdf, 31 pp., including Affidavit of Nathaniel E. Frank-White, submitted as Exhibit 1013 in IPR 2025-00233.
Regeneron Pharmaceuticals, Inc., Presentation, "Merrill Lynch Global Pharmaceutical, Biotechnology and Medical Device Conference" (Feb. 8, 2006), available at https://web.archive.org/web/20060316092133/Http:/www.regeneron.com/investor/Regn_ML_Feb06.pdf, 29 pages, including Affidavit of Nathaniel E. Frank-White, submitted as Exhibit 1012 in IPR 2025-00233.
Regeneron Pharmaceuticals, Inc., Presentation, "UBS Global Life Sciences Conference," 25 pp. (Sep. 27, 2005).
Regeneron Presentation, "VEGF Trap Clinical Trial Update," presented at Angiogenesis 2006, Miami, FL (Feb. 3, 2006), available at

(56) References Cited

OTHER PUBLICATIONS https://web.archive.org/web/20060221025443/http:/www.regeneron.com/investor/Regn_BascomPalmer2006.pdf, 23 pages, including Affidavit of Nathaniel E. Frank-White, submitted as Exhibit 1011 in IPR 2025-00233.
Regeneron Press Release, "Regeneron's VEGF Trap Demonstrates Positive Preliminary Results in Patients with Age-Related Macular Degeneration," 2 pp. (Feb. 2, 2006).
Regeneron Press Release, "VEGF Trap Oncology Program with Sanofi-Aventis Planned to Expand Rapidly," 4 pp. (Sep. 26, 2005).
REMICADE® label (2013) (58 pp.).
REMICADE®, *Physician's Desk Reference*, 59th Ed., Thompson PDR (NJ), pp. 1117-1122 (2005).
Remicade™ Infliximab for IV Injection, Label, 12 pp. (Aug. 12, 1998).
*Remington: The Science and Practice of Pharmacy*, 21st edition, Chapters 18, 19, 39, 41, 43 (May 15, 2005).
Remington's Pharmaceutical Sciences, 18th Edition—Polysorbates (1990) (4 pp.).
Reply of Patentee in Opposition of EP 2944306 (Mar. 20, 2023).
Request for Ex Parte Reexamination of U.S. Pat. No. 10,406,226 (Dix et al.), filed Feb. 11, 2020 (90 pp.).
Request for Ex Parte Reexamination of U.S. Pat. No. 10,464,992 (Furfine et al.), filed Feb. 11, 2020 (78 pp.).
Response to Office Action Under 37 C.F.R. § 1.111 filed Nov.r 22, 2011, in U.S. Appl. No. 12/835,065 (4 pp.).
Resume of Reiner Gentz, Ph.D., as submitted to the USPTO on Jan. 7, 2021, in Inter Partes Review No. IPR2021-00402, 3 pp.
Rezaei et al., "Age-Related Macular Degeneration Drug Delivery," in *Intraocular Drug Delivery*, G. Jaffe et al. (eds), Ch. 16, pp. 249-263 (Taylor & Francis) (ebook published Mar. 12, 2006).
Ribeiro et al., "An Algorithm for the Computer Calculation of the Coefficients of a Polynomial that Allows Determination of Isoelectric Points of Proteins and Other Macromolecules," *Comput. Biol. Med.*, 20(4):235-242 (1990).
Rich et al., "Short-Term Safety and Efficacy of Intravitreal Bevacizumab (Avastin) for Neovascular Age-Related Macular Degeneration," *Retina, The Journal of Retinal and Vitreous Diseases*, 26(5): 495-511 (May 2006).
Riss et al., "Choosing The Right Cell-Based Assay For Your Research," *Cell Notes*, 6:6-12 (2003).
Riss et al., "Use of Multiple Assay Endpoints to Investigate the Effects of Incubation Time, Dose of Toxin, and Plating Density in Cell-Based Cytotoxicity Assays," *ASSAY and Drug Development Technologies*, 2(1):51-75 (2004).
Riss, "Selecting Cell-Based Assays for Drug Discovery Screening," *Cell Notes*, 13:16-21 (2005).
Rixe et al., Abstract 13161, "Safety and pharmacokinetics of intravenous VEGF Trap plus irinotecan, 5-fluorouracil, and leucovorin (I-LV5FU2) in a combination phase I clinical trial of patients with advanced solid tumors," Meeting Abstract: 2006 ASCO Annual Meeting, *Journal of Clinical Oncology*, 24:18(Suppl.), 3 pp. (Jun. 20, 2006).
Ronin et al., "Synthetic Substrates for Thyroid Oligosaccharide Transferase," *Eur. J. Biochem.*, 118(1):159-164 (Aug. 1981).
Rosenfeld et al. "Tolerability and Efficacy of Multiple Escalating Doses of Ranibizumab (Lucentis) for Neovascular Age-Related Macular Degeneration," *Ophthalmology*, 113(4):623-632 (Apr. 2006).
Rosenfeld et al., "Maximum tolerated dose of a humanized anti-vascular endothelial growth factor antibody fragment for treating neovascular age-related macular degeneration," *The American Academy of Ophthalmology*, 112(6):1048-1053 (epub May 9, 2005).
Rosenfeld et al., "RhuFab V2 (Anti-VEGF Antibody Fragment) in neovascular AMD: Safety, tolerability, and efficacy of multiple, escalating dose intravitreal injections," ARVO Annual Meeting Abstract, *Investigative Ophthalmology & Visual Science*, 44:970 (May 4-9, 2003).
Rosenfeld et al., Abstract, "RhuFab V2 Dose-Escalation Trial: Safety and Tolerability of 3 Escalating Dosing Regimens in Subjects with Age-Related Macular Degeneration (AMD)," ASRS 2003 Annual Meeting, New York, pp. 99-100 (5 total pages) (Aug. 16-20, 2003).
Rosenfeld, "Avastin in Ophthalmology: A Global Phenomenon," *American Academy of Ophthalmology*, 5 pp. in English, 2 pp. in Korean (Apr. 1, 2006).
Rosenfeld, "An Update on Bevacizumab," *Review of Ophthalmology*, 1-5 (Jan. 2006).
Routier et al., "The glycosylation pattern of a humanized IgGl antibody (D1.3) expressed in CHO cells," *Glycoconjugate J.*, 14:201-207 (1997).
Rowe et al., "Glycerin," in *Handbook of Pharmaceutical Excipients* (4th Edition), London: Pharmaceutical Press, pp. 257-259 (2003).
Rowe et al., "Mannitol," in *Handbook of Pharmaceutical Excipients* (4th Edition), London: Pharmaceutical Press, pp. 373-377 (2003).
Rowe et al., "Polyethylene Glycol," in Handbook of Pharmaceutical Excipients (4th Edition), London: Pharmaceutical Press, pp. 454-459 (2003).
Rowe et al., "Polyoxyethylene Sorbitan Fatty Acid Esters," in Handbook of Pharmaceutical Excipients (4th Edition), London: Pharmaceutical Press, pp. 479-483 (2003).
Rowe et al., "Potassium Chloride," in Handbook of Pharmaceutical Excipients (4th Edition), London: Pharmaceutical Press, pp. 497-499 (2003).
Rowe et al., "Propylene Glycol," in Handbook of Pharmaceutical Excipients (4th Edition), London: Pharmaceutical Press, pp. 521-523 (2003).
Rowe et al., "Sodium Chloride," in Handbook of Pharmaceutical Excipients (4th Edition), London: Pharmaceutical Press, pp. 556-559 (2003).
Rowe et al., "Sodium Phosphate, Dibasic," in Handbook of Pharmaceutical Excipients (4th Edition), London: Pharmaceutical Press, pp. 574-576 (2003).
Rowe et al., "Sodium Phosphate, Monobasic," in Handbook of Pharmaceutical Excipients (4th Edition), London: Pharmaceutical Press, pp. 577-578 (2003).
Rowe et al., "Sorbitol," in Handbook of Pharmaceutical Excipients (4th Edition), London: Pharmaceutical Press, pp. 596-599 (2003).
Rowe et al., "Sucrose," in Handbook of Pharmaceutical Excipients (4th Edition), London: Pharmaceutical Press, pp. 622-625 (2003).
Rowe et al., "Trehalose," in Handbook of Pharmaceutical Excipients (4th Edition), London: Pharmaceutical Press, pp. 657-658 (2003).
Rudd et al., "Glycosylation: Heterogeneity and the 3D Structure of Proteins," *Critical Reviews in Biochemistry & Molecular Bio.*, 32(1):1-100 (1997).
Rudge et al., "VEGF Trap as a Novel Antiangiogenic Treatment Currently in Clinical Trials for Cancer and Eye Diseases, and VelociGene®-based Discovery of the Next Generation of Angiogenesis Targets," *Cold Spring Harbor Symposia on Quantitative Biology*, 70:411-418 (2005).
Saishin et al., "VEGF-TRAPR1R2 Suppresses Choroidal Neovascularization and VEGF-Induced Breakdown of the Blood-Retinal Barrier," *Journal of Cellular Physiology*, 195:241-248 (2003).
Sakuma et al., "Safety of In Vivo Pharmacologic Vitreolysis with Recombinant Microplasmin in Rabbit Eyes," *Invest. Ophthalmol. Vis. Sci.*, 46(9):3295-3299 (Sep. 2005).
Sebag, "III. Biochemistry of the Vitreous," in *The Vitreous*, Springer-Verlag New York, Inc., NY, p. 26 (1989).
Securities Daily, Announcement of Chengdu Kanghong Pharmaceutical Group Co., Ltd. on stopping the global multi-center clinical trial of Conbercept ophthalmic injection (Apr. 13, 2021) (with English language machine translation), available at <http://cpaper.zqrb.cn/html/2021-04/10/content_716426.htm?div=-1.>.
Semeraro et al., "Aflibercept in wet AMD: specific role and optimal use," *Drug Design, Development and Therapy*, 7:711-722 (Aug. 2, 2013).
Sethuraman et al., "Challenges in therapeutic glycoprotein production," *Current Opinion in Biotechnology*, 17:341-346 (available online Jul. 7, 2006).
Shah et al., "A Double-Masked, Placebo-Controlled, Safety, and Tolerability Study of Intravenous VEGF Trap in Patients with

(56) References Cited

OTHER PUBLICATIONS

Diabetic Macular Edema," ARVO Annual Meeting Abstract (Apr. 30-May 4, 2006), *Investigative Ophthalmology & Visual Science*, 47(13) 3850, 2 pp. (May 2006).

Shahar et al., "Electrophysiologic and retinal penetration studies following intravitreal injection of bevacizumab (Avastin)," *Retina*, 26(3):262-269 (Mar. 2006).

Shukla et al., "Downstream Processing of Fc-Fusion Proteins," *Therapeutic Fc- Fusion Proteins*, 97-114 (2014).

Shukla et al., "Protein aggregation kinetics during Protein A chromatography: Case study for an Fc fusion protein," *Journal of Chromatography A*, 1171:22-28 (2007).

Sigma Polyoxyethylenesorbitan Monolaurate (Tween 20) Product Information, Sigma Prod. Nos. P1379, P7949, and P6585, 3 pp. (May 14, 1997).

Silva Tavares Neto et al., "Intravitreal bevacizumab plus propranolol for neovascular age-related macular degeneration (the BEVALOL study): a phase I clinical trial," *International Journal of Retina and Vitreous*, 9:28, pp. 1-9 (Apr. 13, 2023).

SIMULECT® label, as submitted to the USPTO on January 7, 2021, in Inter Partes Review No. IPR2021-00402 as Exhibit 1028 (1998) (7 pp.).

SIMULECT®, *Physician's Desk Reference*, 59th Ed., Thompson PDR (NJ), pp. 325 & 2367-2369 (2005).

Sinclair et al., "Glycoengineering: The Effect of the Glycosylation on the Properties of Therapeutic Proteins," *J. Pharmaceutical Sciences*, 94(8):1626-1635 (Aug. 2005).

Skidgel, "Structure and function of mammalian zinc carboxypeptidases," in *Zinc Metalloproteases in Health and Disease*, Hooper (ed.), Taylor & Francis, London, pp. 241-283 (ebook published on July 29, 1996).

Sorbera et al., "Ranibizumab: Treatment of Age-Related Macular Degeneration Humanized Monoclonal Anti-VEGF Antibody Angiogenesis Inhibitor," *Drugs of the Future*, 28(6):541-545 (2003).

Souillac, "Biophysical Characterization of Insoluble Aggregates of a Multi-Domain Protein: An Insight into the Role of the Various Domains," Journal of Pharmaceutical Sciences, 94:2069-2083 (2005).

Spaide et al., "Intravitreal Bevacizumab Treatment Of Choroidal Neovascularization Secondary To Age-Related Macular Degeneration," *Retina*, 26(4):383-390 (Apr. 2006).

Stewart, "Clinical and differential utility of VEGF inhibitors in wet age-related macular degeneration: focus on aflibercept," Clinical Ophthalmology, 6:175-1186 (2012).

Stoll et al., "General Methods for Handling Proteins and Enzymes; [4] Buffers: Principles and Practice," in *Methods in Enzymology*, vol. 182, pp, 24-38, Academic Press, Inc. (Mar. 14, 1990).

Strickley et al., "A review of formulations of commercially available antibodies," *Journal of Pharmaceutical Sciences*, 110(7);2590-2608 (published online Mar. 28, 2021).

Strickley, "Solubilizing Excipients in Oral and Injectable Formulations," Pharmaceutical Research, 21(2):201-230 (2004).

Tang, China's Kanghong Pharma Hits Limit Down as France Stops Trials of Ophthalmic Drug, YiCai Global (Mar. 29, 2021) <https://www.yicaiglobal.com/news/china-kanghong-pharma-hits-limit-down-as-france-stops-trials-of-ophthalmic-drug>.

Tezel et al., "Posterior Vitreous Detachment with Dispase," *Retina*, 18(1):7-15 (1998).

The CATT Research Group, "Ranibizumab and Bevacizumab for Neovascular Age-Related Macular Degeneration," *N. Engl. J. Med.*, 364(20):1897-1908 (Epub Apr. 28, 2011).

The Eyetech Study Group, "Anti-vascular Endothelial Growth Factor Therapy for Subfoveal Choroidal Neovascularization Secondary to Age-related Macular Degeneration," *Ophthalmology*, 110(5):979-2986 (May 2003).

Thorpe et al., "The Use of Bioassays for the Characterisation and Control of Biological Therapeutic Products Produced by Biotechnology," *Dev. Biol. Stand*, 91:79-88 (1997).

Treuheit et al., "Inverse relationship of protein concentration and aggregation," *Pharmaceutical Research*, 19(4):511-516 (Apr. 2002).

Trial transcript (unsealed portion), testimony of Eric Furfine during bench trial proceedings in *Regeneron Pharmaceuticals, Inc.* v. *Mylan Pharmaceuticals, Inc. et al.*, Civil Action 1:22-cv-61, held in Clarksburg, West Virginia, pp. 537-568 (Jun. 14, 2023).

Tsui et al., "Ocriplasmin for Vitreoretinal Diseases," *Journal of Biomedicine and Biotechnology*, vol. 2012, Article ID 354979, 6 pp. (Epub Oct. 14, 2012).

U.S. Food & Drug Administration, "Guidance for Industry—Container Closure Systems for Packaging Human Drugs and Biologics," (56 pp.) (May 1999), submitted in IPR2023-00462 as Exhibit 1038.

U.S. Food & Drug Administration, "Guidance for Industry—Q6B Specification: Test Procedures and Acceptance Criteria for Biotechnological/Biological Products," (24 pp.) (Aug. 1999), submitted in IPR2023-00462 as Exhibit 1047.

U.S. Food & Drug Administration, "Guidance for Industry Q1A(R2) Stability Testing of New Drug Substances and Products," as submitted to the USPTO on Jan. 7, 2021, in Inter Partes Review No. IPR2021-00402 as Exhibit 1019 (25 pp.).

U.S. Food & Drug Administration, "Points to Consider in the Manufacture and Testing of Monoclonal Antibody Products for Human Use," pp. 1-50 (Feb. 28, 1997), submitted in IPR2023-00620 as Exhibit 1020.

UniProt database, P01857, available at https://rest.uniprot.org/unisave/P01857?format=txt&versions=64, 4 pp. (May 30, 2006)

UniProt database, P17948, available at https://rest.uniprot.org/unisave/P17948?format=txt&versions=83, 5 pp. (May 30, 2006).

UniProt database, P35968, available at https://rest.uniprot.org/unisave/P35968?format=txt&versions=69, 4 pp. (May 30, 2006).

US Pharmacopeia (excerpt), "<788> Particulate Matter in Injections," Second Interim Revision Announcement 33(2), 19 pp. (Nov. 21, 2016).

US Pharmacopeia (excerpt),"<789> Particulate Matter in Ophthalmic Solutions," (Aug. 1, 2015) and "<790> Visible Particulates in Injections," (May 1, 2016) found at: https://online.uspnf.com/uspnf/document/1_GUID-79EB4754-EA8C-481D-833F-77EF93739DE6_1_en-US, 3 pp. (Feb. 9, 2023).

USPTO Communication on Ex Parte Reexamination of U.S. Pat. No. 10,464,992 USPTO Communication, pp. 1-12, published Apr. 1, 2020.

Van Bruggen et al., "VEGF antagonism reduces edema formation and tissue damage after ischemia/reperfusion injury in the mouse brain," *The Journal of Clinical Investigation*, 104(11):1613-1620 (1999).

Van Slyke, "On the Measurement of Buffer Values and on the Relationship of Buffer Value to the Dissociation Constant of the Buffer and the Concentration and Reaction of the Buffer Solution," *Hospital of The Rockefeller Institute for Medical Research*, 525-570 (1922).

Vandamme, "Microemulsions as ocular drug delivery systems: recent developments and future challenges," *Progress in Retinal and Eye Research*, 21(1):15-34 (Jan. 2002).

Vanhoof et al., "Proline Motifs in Peptides and Their Biological Processing," *The FASEB Journal*, 9(9):736-744 (Jun. 1995).

Vernon, "Intravitreal triamcinolone therapy for diabetic macular oedema," *Br. J. Ophthalmol.*, 89:931-933 (First published Jul. 15, 2005).

Veurink et al., "Breaking the aggregation of the monoclonal antibody bevacizumab (Avastin)," *Pharm. Res.*, 30:1176-1187 (Feb. 15, 2013).

Vial, Merriam-Webster.com, <https://merriam-webster.com/dictionary/vial> (last visited Jan. 16, 2023).

Vial, Merriam-Webster.com, 4 pp. (last updated Nov. 14, 2024).

Vitrase® (Hyaluronidase Injection) Ovine, 200 USP units/mL label, NDS 21-640/S-002 & S-003, pp. 3-8, available at https://www.accessdata.fda.gov/drugsatfda_docs/label/2004/21640s002,0031bl.pdf) (2004).

Vitravene™ Injection, Fomivirsen sodium intravitreal injectable, Draft US Package Insert, 10 pp. (Aug. 26, 1998).

Voight, "Injection and infusion preparations," *Pharmazeutische Technologie*, pp. 461-462 (2006) (with English language translation).

(56) References Cited

OTHER PUBLICATIONS

Voigt , "Pharmazeutische Technologie: Fur Studium und Beruf," 10th edition, Deutscher Apotheker Verlag, Stuttgart, pp. 461-462 (Excerpt), 4 pp. with English translation (4 pp.) (2006).
Von Heijne, "Patterns of amino acids near signal-Sequences Cleavage Sites," *Eur. J. Biochem.*, 133(1):17-21 (Jun. 1983).
Von Heijne, "Signal sequences, The limits of Variation," *J. Mol. Biol.*, 184(1):99-105 (Jul. 5, 1985).
Von Heijne, "A new method for predicting signal sequence cleavage sites," *Nucleic Acids Research*, 14(11):4683-4690 (Jun. 11, 1986).
Von Heijne, "The Signal Peptide," *Journal of Membrane Biology*, 115:195-201 (May 1990).
Wang et al., "Safety and Efficacy of Dispase and Plasmin in Pharmacologic Vitreolysis," *Investigative Ophthalmology & Visual Science*, 45(9):3286-3290 (Sep. 2004).
Wang et al., "Antibody Structure, Instability, and Formulation," *Journal of Pharmaceutical Sciences*, 96(1), pp. 1-26 (published online in Wiley Interscience (www.interscience.wiley.com)) (Jan. 2007).
Wang et al., "Glycoengineering of CHO cells to improve product quality," Paula Meleady (ed.), *Heterologous Protein Production in CHO Cells: Methods and Protocols, Methods in Molecular Biology*, vol. 1603:25-44, DOI 10.1007/978-1-4939-6972-2_2, © Springer Science+Business Media LLC (2017).
Wang, "Instability, stabilization, and formulation of liquid protein pharmaceuticals," International Journal of Pharmaceutics, 185:129-188 (1999).
Wang, "Lyophilization and Development of Solid Protein Pharmaceuticals," International Journal of Pharmaceutics, 203:1-60 (2000).
Wang, "Protein aggregation and its inhibition in biopharmaceutics," International Journal of Pharmaceutics, 289:1-30 (2005).
Webb et al., "A new mechanism for decreasing aggregation of recombinant human interferon-gamma by a surfactant: slowed dissolution of lyophilized formulations in a solution containing 0.03% polysorbate 20," *J. Pharm. Sci.*, 93(10):2609-2623 (2002).
Weisbecker et al. (eds.), *Physicians' Desk Reference for Ophthalmology*, 28th edition "Intraocular Product Information," p. 318-319 pp. (2000).
White et al., "Best practices in bioassay development to support registration of biopharmaceuticals," *BioTechniques*, 67(3):126-137 (2019).
WHO Drug Information, "International Nonproprietary Names for Pharmaceutical Substances (INN)," *WHO Drug information*, vol. 21, No. 1, List 57, pp. 53-56 (2007).
Wiegand et al., "Long-lasting Inhibition of Corneal Neovascularization following Systemic Administration of the VEGF Trap," ARVO Annual Meeting Abstract, *Invest. Ophthalmol. Visual Sci.*, 44(13):829, 2 pp. (May 2003).
Wiegand et al., "VEGF Trap Both Prevents Experimental Choroidal Neovascularization and Causes Regression of Established Lesions in Non-Human Primates," ARVO Annual Meeting Abstract, *Invest. Ophthalmol. Visual Sci.*, 46:1411, 2 pp. (May 2005).
Wigent et al., "Chemical Kinetics," in *Remington: The Science and Practice of Pharmacy* (21st ed.), Martin (ed.), Ch. 19, pp. 266-279 (Lippincott Williams & Wilkins) (May 15, 2005).
Winter et al., "Man-made antibodies," *Nature*, 349:293-299 (1991).
Wulff et al., "Prevention of Thecal Angiogenesis, Antral Follicular Growth, and Ovulation in the Primate by Treatment with Vascular Endothelial Growth Factor Trap R1R2," *Endocrinology*, 143(7):2797-2807 (2002).
Wurm et al., "Optimizing Production and Recovery of Immunoadhesins," in *Antibody Fusion Proteins*, Chamow et al. (eds.), Wiley-0Liss (A John Wiley & Sons, Inc. publication), New York, NY, Chapter 10 and Index, pp. 281-308 and 309-312 (Apr. 13, 1999).
Wurm, "Production of Recombinant Protein Therapeutics in Cultivated Mammalian Cells," *Nature Biotechnology*, 22(11):1393-1398 (Nov. 2004).
XOLAIR® label (2003) (17 pp.)

XOLAIR®, *Physician's Desk Reference*, 59th Ed., Thompson PDR (NJ), pp. 1359-1362 (2005).
Yoshitsugu et al., "VEGF-TRAP$_{R1R2}$ Suppresses Choroidal Neovascularization and VEGF-Induced Breakdown of the Blood-Retinal Barrier," *J. Cell. Physiol.*, 195:241-248 (Mar. 12, 2003).
Yost et al., "A stop transfer sequence confers predictable transmembrane orientation to a previously secreted protein in cell-free systems," *Cell*, 34(3):759-766 (Oct. 1983).
Young et al., "Safety and efficacy of intravitreal triamcinolone for cystoid macular oedema in uveitis," *Clinical and Experimental Ophthalmology*, 29(1):2-6 (Feb. 2001).
Zaltrap, Summary of Product Characteristics in Dutch, 47 pp., with English machine translation (48 pp.), as submitted in related Netherlands Impeachment proceeding C/09/675574 and C/09/675547 on Feb. 5, 2025.
Zaltrap® (ziv-aflibercept), FDA Marketing Information, Initial US Approval 2012, 17 pp.
Zhao et al., "Increasing the homogeneity, stability and activity of human serum albumin and interferon-α2b fusion protein by linker engineering," *Protein Expression and Purification*, 61:73-77 (2008).
Zimmer et al., "Safety Evaluation Of Intravitreal Administration of VEGF Trap in Cynomolgus Monkeys for 13 Weeks," ARVO Annual Meeting Abstract, *Investigative Ophthalmology & Visual Science*, 47(13):1751 (May 2006).
Decision Granting Institution of Inter Partes Review in *Celltrion, Inc. v.Regeneron Pharmaceuticals, Inc.*, IPR2023-00462 (Jul. 20, 2023).
Rosenfeld et al., "Optical Coherence Tomography Findings after an Intravitreal Injection of Bevacizumab (Avastin®) for Neovascular Age-Related Macular Degeneration," *Ophthalmic Surgery, Lasers & Imaging*, 36(4):331-335 (Jul./Aug. 2005).
Rosenfeld et al., "Optical Coherence Tomography Findings after an Intravitreal Injection of Bevacizumab (Avastin®) for Macular Edema from Central Retinal Vein Occlusion," *Ophthalmic Surgery, Lasers & Imaging*, 36(4):336-339 (Jul./Aug. 2005).
Order Granting Motion for Preliminary Injunction (redacted), dated Jun. 21, 2024, In Re: Aflibercept Patent Litigation, Case No. 1:23-CV-97.
Order Denying Regeneron's Motion for Preliminary Injunction (redacted), dated Sep. 23, 2024, In. re: Aflibercept Patent Litigation, Case No. 1:23-CV-39.
Order Granting Motions for Preliminary Injunction (redacted) dated Jun. 14, 2024, In re: Aflibercept Patent Litigation, Case Nos. 1:23-CV-94 and 1:23-CV-106.
Order Granting Motion for Preliminary Injunction (redacted) dated Jun. 28, 2024, In Re: Aflibercept Patent Litigation, Case No. 1:23-CV-89.
Bevacizumab, Summary of Product characteristics in English, 76 pp., submitted as Exhibit EP13 in Netherlands revocation action, proceedings No. C/09/675574 and C/09/675547 on Nov. 13, 2024.
Carbowax™ Polyethylene Glycol (PEG) 3350 (1 pg.), submitted as Exhibit 1049 in PGR2021-00117 on Sep. 7, 2021.
KEGG (Kyoto Encyclopedia of Genes and Genomes) Product Information Sheet for Aflibercept (1 pg.), submitted as Exhibit 1072 in PGR2021-00117 on Sep. 7, 2021.
Perrin et al., "1.1 The concept of buffer action," in *Buffers for pH and Metal Ion Control*, Chapman and Hall Ltd. (London), Perrin et al. (eds.), pp. 1-2 (1974).
Pre-filled Syringe, Collins Dictionary, https://www.collinsdictionary.com/de/worterbuch/englisch/pre-filled-syringe, submitted as Exhibit D46 in Opposition of EP 2944306 on Mar. 20, 2023.
U.S. Court of Appeals for the Federal Circuit Order in *Regeneron Pharmaceuticals, Inc. v. Mylan Pharmaceuticals Inc et al.*, Case 24-1965, Jan. 29, 2025.
U.S. Court of Appeals for the Federal Circuit Order in *Regeneron Pharmaceuticals, Inc. v. Mylan Pharmaceuticals Inc et al.*, Case 24-2009, Jan. 29, 2025.
U.S. Court of Appeals for the Federal Circuit Order in *Regeneron Pharmaceuticals, Inc. v. Mylan Pharmaceuticals Inc et al.*, Case 24-2058, Mar. 5, 2025.
U.S. Court of Appeals for the Federal Circuit Order in *Regeneron Pharmaceuticals, Inc. v. Mylan Pharmaceuticals Inc et al.*, Case 24-2351, Mar. 14, 2025.

(56) References Cited

OTHER PUBLICATIONS

Ahmadieh et al., "Rapid regression of extensive retinovitreal neovascularization secondary to branch retinal vein occlusion after a single intravitreal injection of bevacizumab," *Int. Ophthalmol.*, 26(4-5):191-193 (Aug.-Oct. 2005), Epub Feb. 8, 2007.

Aiello et al., "Supression of retinal neovascularization in vivo by inhibition of vascular endothelial growth factor (VEGF) using soluble VEGF-receptor chimeric proteins," *Proc. Natl. Acad. Sci. USA*, 92(23):10457-10461. (Nov. 7, 1995).

Bro et al., "Off-label use of bevacizumab for wet age-related macular degeneration in Europe," *Graefes Arch. Clin. Exp. Ophthalmol.*, 258(3):503-511 (Mar. 2020).

Goossens et al., "Avastin (bevacizumab), Macugen (pegaptanib) en Lucentis (ranibizumab): vergelijking van medicatiekosten," ("Avastin (bevacizumab), Macugen (pegatanib) and Lucentis (ranibizumab): comparison of medication costs"), with English Abstract, *PW Wetenschappelijk Platform.*, 2(4):75-79 (2008).

Lawrence, "Polyoxyethlene Sorbitan Fatty Acid Esters" in Rowe et al. (eds), *Handbook of Pharmaceutical Excipients*, Fifth Edition, Pharmaceutical Press, London, UK, pp. 580-584 (2006).

Liu et al., "Freeze-drying of protein from a sucrose-glycine excipient system: effect of formulation composition on the initial recovery of protein activity," *AAPS PharmSciTech.*, 6(2):E150-E157, Article 23 (Sep. 30, 2005).

Lytenava SmPC, "Annex I, Summary of Product Characteristics," 27 pp., date of first authorization: May 27, 2024.

Michels et al., "Therapie der neovaskulären altersbedingten Makuladegeneration mit Ranibizumab/Lucentis™,"(Treatment of Neovascular Age-Related Macular Degeneration with Ranibizumab/Lucentis™), with English Abstract, *Klinische Monatsblatter fur Augenheilkunde*, 222(6):480-484 (2005).

National Institutes of Health (NIH), "Long-term benefits of age-related macular degeneration treatments," 3 pp. (May 10, 2016).

Osterberg et., "Development of freeze-dried albumin-free formulation of recombinant factor VIII SQ," *Pharm. Res.*, 14(7):892-898 (Jul. 1997).

Regeneron Form 8-K, including Press release, "Regeneron reports positive phase I data for the VEGF Trap in age-related macular degeneration," 8 pp. (May 1, 2006).

Reichel, "Intravitreal bevacizumab for choroidal neovascularization and cystoid macular edema: a cost-effective treatment?," *Ophthalmic Surg. Lasers Imaging*, 36(4):270-2711 (Jul.-Aug. 2005).

Singh et al., "Targeting VEGF in AMD, Anti-VEGF treatments have revolutionized AMD Therapy," Eyetube Retina Series, 10 pp. (Mar. 2006).

VEGF ANTAGONIST FORMULATIONS SUITABLE FOR INTRAVITREAL ADMINISTRATION

CROSS-REFERENCE TO RELATED APPLICATIONS

This application is a continuation application of U.S. patent application Ser. No. 18/344,786 filed Jun. 29, 2023, which is a continuation of U.S. patent application Ser. No. 17/348,438 filed Jun. 15, 2021, which issued as U.S. Pat. No. 11,732,024 on Aug. 22, 2023, which is a continuation of U.S. patent application Ser. No. 16/582,486 filed Sep. 25, 2019, which issued as U.S. Pat. No. 11,066,458 on Jul. 20, 2021, which is a continuation of U.S. patent application Ser. No. 16/159,269 filed Oct. 12, 2018, which issued as U.S. Pat. No. 10,464,992 on Nov. 5, 2019, which is a continuation of U.S. patent application Ser. No. 15/879,294 filed Jan. 24, 2018, which issued as U.S. Pat. No. 10,400,025 on Sep. 3, 2019, which is a continuation of U.S. patent application Ser. No. 15/095,606 filed Apr. 11, 2016, which issued as U.S. Pat. No. 9,914,763 on Mar. 13, 2018, which is a continuation of U.S. patent Application Ser. No. 14/330,096, filed Jul. 14, 2014, which issued as U.S. Pat. No. 9,340,594 on May 17, 2016, which is a continuation of U.S. patent application Ser. No. 13/914,996, filed Jun. 11, 2013, which issued as U.S. Pat. No. 8,802,107 on Aug. 12, 2014, which is a continuation application of U.S. patent application Ser. No. 13/329,770, filed Dec. 19, 2011, which issued as U.S. Pat. No. 8,481,046 on Jul. 9, 2013, which is a continuation application of U.S. patent application Ser. No. 12/833,417, filed Jul. 9, 2010, which issued as U.S. Pat. No. 8,092,803 on Jan. 10, 2012, which is a continuation application of U.S. patent application Ser. No. 12/560,885, filed Sep. 16, 2009, which issued as U.S. Pat. No. 7,807,164 on Oct. 5, 2010, which is a divisional application of U.S. patent application Ser. No. 11/818,463, filed Jun. 14, 2007, which issued as U.S. Pat. No. 7,608,261 on Oct. 27, 2009, which claims the benefit under 35 U.S.C. § 119(e) of U.S. Provisional Application No. 60/814,484, filed Jun. 16, 2006, which applications are each hereby incorporated by reference.

INCORPORATION OF SEQUENCE LISTING

A sequence listing contained in the file named P35063US15_Seq_Listing.xml, which is 9,739 bytes in size (measured in MS-Windows®) and was created on Oct. 23, 2024, is filed electronically herewith and is herein incorporated by reference in its entirety.

BACKGROUND OF INVENTION

Field of the Invention

The present invention is directed to pharmaceutical formulations suitable for intravitreal administration comprising agents capable of inhibiting vascular endothelial growth factor (VEGF), and to methods for making and using such formulations. The invention includes liquid pharmaceutical formulations having increased stability, as well as formulations that may be lyophilize and reconstituted for intravitreal administration.

Statement of Related Art

Vascular endothelial growth factor (VEGF) expression is nearly ubiquitous in human cancer, consistent with its role as a key mediator of tumor neoangiogenesis. Blockade of VEGF function, by binding to the molecule or its VEGFR-2 receptor, inhibits growth of implanted tumor cells in multiple different xenograft models (see, for example, Gerber et al. (2000) Cancer Res. 60:6253-6258). A soluble VEGF-specific fusion protein antagonist, termed a "VEGF trap" has been described (Kim et al. (2002) Proc. Natl. Acad. Sci. USA 99:11399-404; Holash et al. (2002) Proc. Natl. Acad. Sci. USA 99:11393-8), which applications are specifically incorporated by reference in their entirety.

Ophthalmic formulations are known, see for example, U.S. Pat. Nos. 7,033,604 and 6,777,429. An ophthalmic formulation of a VEGF antibody is described in U.S. Pat. No. 6,676,941.

Lyophilization (freeze drying under controlled conditions) is commonly used for long-term storage of proteins. The lyophilized protein is substantially resistant to degradation, aggregation, oxidation, and other degenerative processes while in the freeze-dried state (see, for example, U.S. Pat. No. 6,436,897).

BRIEF SUMMARY OF THE INVENTION

Stable formulations of a VEGF-specific fusion protein antagonist are provided. Pharmaceutically acceptable formulations are provided that comprise a VEGF "trap" antagonist with a pharmaceutically acceptable carrier. In specific embodiments, liquid and lyophilized formulations are provided.

In a first aspect, a stable liquid ophthalmic formulation of a VEGF-specific fusion protein antagonist is provided, comprising a fusion protein that comprises a receptor component consisting essentially of an immunoglobulin-like (Ig) domain 2 of a first VEGF receptor and Ig domain 3 of a second VEGF receptor, and a multimerizing component (also termed a "VEGF trap"). In a specific embodiment of the VEGF-specific fusion protein antagonist, the first VEGF receptor is Flt1 and the second VEGF receptor is Flk1 or Flt4. In a more specific embodiment the fusion protein has the amino acid sequence of SEQ ID NO:2 or SEQ ID NO:4. Preferably, the VEGF antagonist is a dimer comprising two fusion proteins of SEQ ID NO:4.

In one aspect, a stable liquid ophthalmic formulation is provided that comprises 1-100 mg/ml VEGF-specific fusion protein antagonist, 0.01-5% of one or more organic co-solvent(s), 30-150 mM of one or more tonicity agent(s), 5-40 mM of a buffering agent, and optionally, 1.0-7.5% of a stabilizing agent, pH between about 5.8-7.0.

In one or more specific embodiments, the organic co-solvent may be polysorbate, for example, polysorbate 20 or polysorbate 80, polyethylene glycol (PEG), for example, PEG 3350, or propylene glycol, or a combination thereof; the tonicity agent may be, for example, sodium chloride or potassium chloride; the stabilizing agent may be sucrose, sorbitol, glycerol, trehalose, or mannitol; and the buffering agent may be, for example, phosphate buffer. In a specific embodiment, the phosphate buffer is a sodium phosphate buffer.

In various embodiments, the organic co-solvent is polysorbate and/or PEG, the stabilizing agent is sucrose, the buffering agent is phosphate buffer, and the tonicity agent is sodium chloride.

More specifically, the stable liquid ophthalmic formulation comprises about 40-50 mg/ml of the VEGF antagonist (SEQ ID NO:4), about 10 mM phosphate buffer, 0.01-3% polysorbate and/or PEG, 40-135 mM sodium chloride, and optionally 5.0% sucrose, pH about 6.2-6.3.

In a specific preferred embodiment, the stable liquid ophthalmic formulation comprises about 50 mg/ml of the VEGF antagonist (SEQ ID NO:4), 10 mM sodium phosphate buffer, 50 mM sodium chloride, 0.1% polysorbate, and 5% sucrose, pH about 6.2-6.3.

In a specific preferred embodiment, the stable liquid ophthalmic formulation comprises about 50 mg/ml of the VEGF antagonist (SEQ ID NO:4), 10 mM sodium phosphate buffer, 50 mM sodium chloride, 3% PEG, and 5% sucrose, pH about 6.2-6.3.

In a specific preferred embodiment, the stable liquid ophthalmic formulation comprises about 40 mg/ml of the VEGF antagonist (SEQ ID NO:4), 10 mM sodium phosphate buffer, 40 mM sodium chloride, 0.03% polysorbate, and 5% sucrose, pH about 6.2-6.3.

In a specific preferred embodiment, the stable liquid ophthalmic formulation comprises about 40 mg/ml of the VEGF antagonist (SEQ ID NO:4), 10 mM sodium phosphate buffer, 135 mM sodium chloride, and 0.03% polysorbate, pH about 6.2-6.3.

In another aspect, a stable liquid ophthalmic formulation is provided that comprises 1-100 mg/ml VEGF-specific fusion protein antagonist; 0.01-5% of one or more organic co-solvent(s); 5-40 mM of a buffering agent; and optionally 30-150 mM of one or more tonicity agent(s) and/or 1.0-7.5% of a stabilizing agent; having a pH between about 5.8-7.0.

In various embodiments, the VEGF antagonist (SEQ ID NO:4) is present at a concentration of about 10 to about 80 mg/ml. In various embodiments, the VEGF antagonist (SEQ ID NO:4) is present at a concentration of about 10, about 20, about 30, about 40, about 50, about 60, about 70, or about 80 mg/ml. In a preferred embodiment, the VEGF antagonist (SEQ ID NO:4) is present at a concentration of about 40 mg/ml.

In another embodiment, the stabilizing agent is selected from one or more of sucrose, sorbitol, glycerol, trehalose, and mannitol.

In another embodiment, the organic co-solvent is selected from one or more of polysorbate, for example, polysorbate 20 or polysorbate 80, polyethylene glycol (PEG), for example, PEG 3350, and propylene glycol.

In another embodiment, the buffer is a phosphate buffer, for example, sodium phosphate.

In another embodiment, the tonicity agent is a salt, for example, sodium chloride.

In one embodiment, the stable liquid ophthalmic formulation comprises 10 mM sodium phosphate buffer, about 0.03 to about 0.1% polysorbate and/or about 3% PEG or propylene glycol, about 40 mM sodium chloride, and about 5% sucrose. In a specific embodiment, the stable liquid ophthalmic formulation comprises 10 mM sodium phosphate buffer, about 0.03% polysorbate, about 40 mM sodium chloride, and about 5% sucrose. In another specific embodiment, the pH of the formulation is about 6.2 to about 6.3. In another specific embodiment, the pH is achieved by mixing mono- and dibasic sodium phosphate to the desired pH without acid/base titration.

In a specific embodiment, the stable liquid ophthalmic formulation consists essentially of a VEGF antagonist (SEQ ID NO:4) at 40 mg/ml, 10 mM sodium phosphate buffer, polysorbate at 0.03%, sodium chloride at 40 mM, and sucrose at 5%, pH 6.2-6.3.

In another aspect, a stable liquid ophthalmic formulation is provided that comprises about 10 to about 80 mg/ml VEGF antagonist, about 10 mM sodium phosphate buffer, about 0.03% polysorbate, and about 135 mM sodium chloride, pH 6.2 to 6.3.

In various embodiments, the VEGF antagonist (SEQ ID NO:4) is present at a concentration of about 10 to about 80 mg/ml. In various embodiments, the VEGF antagonist (SEQ ID NO:4) is present at a concentration of about 10, about 20, about 30, about 40, about 50, about 60, about 70, or about 80 mg/ml. In a specific embodiment, the VEGF antagonist (SEQ ID NO:4) is present at a concentration of about 40 mg/ml.

In one embodiment, the stable liquid ophthalmic formulation comprises 40 mg/ml of VEGF antagonist (SEQ ID NO:4), 10 mM sodium phosphate buffer, 0.03% polysorbate, and 135 mM sodium chloride at pH 6.2-6.3. In a specific embodiment, the stable liquid ophthalmic formulation consists essentially of 40 mg/ml of VEGF antagonist (SEQ ID NO:4), 10 mM sodium phosphate buffer, 0.03% polysorbate, and 135 mM sodium chloride at pH 6.2-6.3.

In another aspect, a lyophilizable formulation of a VEGF antagonist is provided, wherein upon lyophilization followed by reconstitution, a stable liquid ophthalmic formulation as described herein is obtained.

In another aspect, a lyophilizable formulation of a vascular endothelial growth factor (VEGF)-specific fusion protein antagonist is provided, comprising 5-50 mg/ml of the VEGF antagonist, 5-25 mM buffer, such as phosphate buffer, 0.01 to 0.15% of one or more of an organic co-solvent, such as polysorbate, propylene glycol and/or PEG, and optionally 1-10% of a stabilizing agent such as sucrose, sorbitol, trehalose, glycerol, or mannitol, pH about 5.8-7.0. In various embodiments, the VEGF antagonist (SEQ ID NO:4) is present at about 5, about 10, about 20, about 30, or about 40 mg/ml. In a specific embodiment, the lyophilizable ophthalmic formulation of the invention comprises 20 mg/ml of the VEGF antagonist, 10 mM sodium phosphate buffer, 0.03% polysorbate, 0.1% PEG, and 2.5% sucrose, pH about 6.2-6.3. In further embodiments, the lyophilizable formulation further comprises sodium chloride. In a specific embodiment, the sodium chloride is present at a concentration of about 20 mM. In another specific embodiment, the sodium chloride is present at a concentration of about 67.5 mM.

In another specific embodiment, the lyophilizable ophthalmic formulation of the invention comprises 20 mg/ml of the VEGF antagonist, 5 mM sodium phosphate buffer, 0.015% polysorbate, 20 mM sodium chloride, and 2.5% sucrose, pH about 6.2-6.3.

In another embodiment, the lyophilizable ophthalmic formulation comprises 5 mg/ml, 10 mg/ml, or 40 mg/ml VEGF antagonist, 5 mM sodium phosphate buffer, 0.015% polysorbate, 20 mM sodium chloride, and 2.5% sucrose, at pH 6.2-6.3. In a specific embodiment, the lyophilizable ophthalmic formulation consists essentially of 5 mg/ml, 10 mg/ml, or 40 mg/ml VEGF antagonist (SEQ ID NO:4), 5 mM sodium phosphate buffer, 0.015% polysorbate, 20 mM sodium chloride, and 2.5% sucrose, at pH 6.2-6.3.

In another specific embodiment, the lyophilizable ophthalmic formulation comprises 20 mg/ml of the VEGF antagonist, 5 mM sodium phosphate buffer, 0.015% polysorbate, and 67.5 mM sodium chloride, pH about 6.2-6.3. In a more specific embodiment, the lyophilizable ophthalmic formulation consists essentially of 20 mg/ml of the VEGF antagonist (SEQ ID NO:4), 5 mM sodium phosphate buffer, 0.015% polysorbate, and 67.5 mM sodium chloride, pH 6.2-6.3.

In another specific embodiment, the lyophilizable ophthalmic formulation comprises 5 mg/ml, 10 mg/ml, or 40 mg/ml VEGF antagonist, 5 mM sodium phosphate buffer, 0.015% polysorbate, and 67.5 mM sodium chloride, pH about 6.2-6.3. In a more specific embodiment, the lyophilizable ophthalmic formulation consists essentially of 5 mg/ml, 10 mg/ml, or 40 mg/ml VEGF antagonist (SEQ ID NO:4), 5 mM sodium phosphate buffer, 0.015% polysorbate, and 67.5 mM sodium chloride, pH about 6.2-6.3.

Generally, the reconstituted formulation is about 2 times the concentration of the pre-lyophilized formulation, e.g., a 20 mg fusion protein/ml pre-lyophilized formulation is reconstituted to a final formulation of 40 mg fusion protein/ml.

Generally, the lyophilized formulation is reconstituted with sterile water suitable for injection. In one embodiment, the reconstitution liquid is bacteriostatic water.

In another aspect, the invention features a method of producing a lyophilized formulation of a VEGF-specific fusion protein antagonist, comprising subjecting the lyophilizable formulation of the invention to lyophilization to generate a lyophilized formulation. The lyophilized formulation may be lyophilized by any method known in the art for lyophilizing a liquid.

In another related aspect, the invention features a method of producing a reconstituted lyophilized formulation of a VEGF antagonist, comprising reconstituting the lyophilized formulation of the invention to a reconstituted formulation. In one embodiment, the reconstituted formulation is twice the concentration of the pre-lyophilized formulation, e.g., the method of the invention comprises: (a) producing a pre-lyophilized formulation of a VEGF-specific fusion protein antagonist, (b) subjecting the pre-lyophilized formulation of step (a) to lyophilization; and (c) reconstituting the lyophilized formulation of step (b).

The invention further features ophthalmic formulations provided in a pre-filled syringe or vial, particularly suitable for intravitreal administration.

Other objects and advantages will become apparent from a review of the ensuing detailed description.

DETAILED DESCRIPTION OF THE INVENTION

The present invention is not limited to particular methods, and experimental conditions described, as such methods and conditions may vary. It is also to be understood that the terminology used herein is for the purpose of describing particular embodiments only, and is not intended to be limiting unless indicated, since the scope of the present invention will be limited only by the appended claims.

Unless stated otherwise, all technical and scientific terms and phrases used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned herein are incorporated herein by reference.

General Description

Safe handling and administration of formulations comprising proteins represent significant challenges to pharmaceutical formulators. Proteins possess unique chemical and physical properties that present stability problems: a variety of degradation pathways exist for proteins, implicating both chemical and physical instability. Chemical instability includes deamination, aggregation, clipping of the peptide backbone, and oxidation of methionine residues. Physical instability encompasses many phenomena, including, for example, aggregation and/or precipitation.

Chemical and physical stability can be promoted by removing water from the protein. Lyophilization (freeze-drying under controlled conditions) is commonly used for long-term storage of proteins. The lyophilized protein is substantially resistant to degradation, aggregation, oxidation, and other degenerative processes while in the freeze-dried state. The lyophilized protein may be reconstituted with water optionally containing a bacteriostatic preservative (e.g., benzyl alcohol) prior to administration.

Definitions

The term "carrier" includes a diluent, adjuvant, excipient, or vehicle with which a composition is administered. Carriers can include sterile liquids, such as, for example, water and oils, including oils of petroleum, animal, vegetable or synthetic origin, such as, for example, peanut oil, soybean oil, mineral oil, sesame oil and the like.

The term "excipient" includes a non-therapeutic agent added to a pharmaceutical composition to provide a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "lyophilized" or "freeze-dried" includes a state of a substance that has been subjected to a drying procedure such as lyophilization, where at least 90% of moisture has been removed.

VEGF Antagonists

A VEGF antagonist is a compound capable of blocking or inhibiting the biological action of vascular endothelial growth factor (VEGF), and includes fusion proteins capable of trapping VEGF. In a preferred embodiment, the VEGF antagonist is the fusion protein of SEQ ID NO:2 or 4; more preferably, SEQ ID NO:4. In specific embodiments, the VEGF antagonist is expressed in a mammalian cell line such as a CHO cell and may be modified post-translationally. In a specific embodiment, the fusion protein comprises amino acids 27-457 of SEQ ID NO:4 and is glycosylated at Asn residues 62, 94, 149, 222 and 308. Preferably, the VEGF antagonist is a dimer composed of two fusion proteins of SEQ ID NO:4.

The VEGF antagonist of the methods and formulations of the invention can be prepared by any suitable method known in the art, or that comes to be known. The VEGF antagonist is preferably substantially free of protein contaminants at the time it is used to prepare the pharmaceutically acceptable formulation. By "substantially free of protein contaminants" is meant, preferably, that at least 90% of the weight of protein of the VEGF-specific fusion protein antagonist preparation used for making a formulation is VEGF fusion protein antagonist protein, more preferably at least 95%, most preferably at least 99%. The fusion protein is preferably substantially free of aggregates. "Substantially free of aggregates" means that at least 90% of the weight of fusion protein is not present in an aggregate at the time the fusion protein is used to prepare the pharmaceutically effective formulation. Unless stated otherwise, the phosphates employed are sodium phosphates and a desired buffering pH is achieved by mixing appropriate amounts of mono- and dibasic sodium phosphate.

Stable Liquid Ophthalmic Formulations

In one aspect, the invention provides a stable pharmaceutically acceptable formulation comprising a VEGF antagonist, wherein the formulation is a liquid formulation suitable for ophthalmic use. Preferably, the liquid formulation comprises a pharmaceutically effective amount of the VEGF antagonist. The formulation can also comprise one or more pharmaceutically acceptable carriers, buffers, tonicity agents, stabilizers, and/or excipients. An example of a pharmaceutically acceptable liquid formulation comprises a VEGF antagonist in a pharmaceutically effective amount, a buffer, an organic co-solvent such as polysorbate, a tonicity agent such as NaCl, and optionally, a stabilizer such as sucrose or trehalose.

Stability is determined in a number of ways at specified time points, including determination of pH, visual inspection of color and appearance, determination of total protein content by methods known in the art, e.g., UV spectroscopy, and purity is determined by, for example, SDS-PAGE, size-exclusion HPLC, bioassay determination of activity, isoelectric focusing, and isoaspartate quantification. In one example of a bioassay useful for determining VEGF antagonist activity, a BAF/3 VEGFR1/EPOR cell line is used to determine VEGF165 binding by the VEGF antagonist of the invention.

Liquid formulations can be stored in an oxygen-deprived environment. Oxygen-deprived environments can be generated by storing the formulations under an inert gas such as, for example, nitrogen or argon. Liquid formulations are preferably stored at about 5° C.

Ophthalmic Lyophilized Formulations

In one aspect of the invention, an ophthalmically acceptable formulation comprising a VEGF antagonist is provided, wherein the formulation is a lyophilizable formulation. Lyophilizable formulations can be reconstituted into solutions, suspensions, emulsions, or any other suitable form for administration or use. Lyophilizable formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill in the art, and typically includes sublimation of water from a frozen formulation under controlled conditions.

Lyophilized formulations can be stored at a wide range of temperatures. Lyophilized formulations may be stored below 25° C., for example, refrigerated at 2-8° C., or at room temperature (e.g., approximately 25° C.). Preferably, lyophilized formulations are stored below about 25° C., more preferably, at about 4-20° C.; below about 4° C.; below about −20° C.; about −40° C.; about −70° C., or about −80° C. Stability of the lyophilized formulation may be determined in a number of ways known to the art, for example, by visual appearance of the cake and/or by moisture content.

Lyophilized formulations are typically reconstituted for use by addition of an aqueous solution to dissolve the lyophilized formulation. A wide variety of aqueous solutions can be used to reconstitute a lyophilized formulation. Preferably, lyophilized formulations are reconstituted using water. Lyophilized formulations are preferably reconstituted with a solution consisting essentially of water (e.g., USP WFI, or water for injection) or bacteriostatic water (e.g., USP WFI with 0.9% benzyl alcohol). However, solutions comprising buffers and/or excipients and/or one or more pharmaceutically acceptable carries can also be used.

Freeze-dried or lyophilized formulations are typically prepared from liquids, that is, from solutions, suspensions, emulsions, and the like. Thus, the liquid that is to undergo freeze-drying or lyophilization preferably comprises all components desired in a final reconstituted liquid formulation. As a result, when reconstituted, the freeze-dried or lyophilized formulation will render a desired liquid formulation upon reconstitution.

EXAMPLES

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only to the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

Example 1. Stability of 50 mg/ml VEGF Trap Liquid Formulation Stored at 5° C. in 3 ml Glass Vials An ophthalmic liquid formulation containing 50 mg/ml VEGF Trap (SEQ ID NO:4), 10 mM phosphate, 50 mM NaCl, 0.1% polysorbate 20, 5% sucrose, and pH 6.25, was stored at 5° C. in 3 ml glass vials and samples tested at 3, 6, 9, 12, 18 and 24 months. Stability was determined by SE-HPLC. The results are shown in Table 1. Turbidity was measured at $OD_{405}$ nm; and percent recovered protein and purity by size exclusion HPLC.

TABLE 1

Stability of 50 mg/ml VEGF Trap Protein (VGFT-SS065)

| Months | Visual Appearance | Turbidity ($OD_{405}$ nm) | pH | % VEGF Trap Recovered | % VEGF Trap Native Configuration |
|---|---|---|---|---|---|
| 0 | Pass | 0.00 | 6.2 | 100 | 98.8 |
| 3 | Pass | 0.00 | 6.2 | 101 | 98.7 |
| 6 | Pass | 0.01 | 6.3 | 100 | 98.3 |
| 9 | Pass | 0.01 | 6.3 | 101 | 98.3 |
| 12 | Pass | 0.01 | 6.3 | 104 | 98.4 |
| 18 | Pass | 0.01 | 6.3 | 96 | 98.1 |
| 24 | Pass | 0.01 | 6.3 | 105 | 98.1 |

Example 2. Stability of 50 mg/ml VEGF Trap Liquid Formulation Stored at 5° C. in 3 ml Glass Vials A liquid formulation containing 50 mg/ml VEGF Trap (SEQ ID NO:4), 10 mM phosphate, 50 mM NaCl, 3% polyethylene glycol 3350, 5% sucrose, and pH 6.25, was stored at 5° C. in 3 nil glass vials and samples tested at 3, 6, 9, 12, 18 and 24 months. Stability results are shown in Table 2. Turbidity, percent recovered protein and purity was determined as described above.

TABLE 2

Stability of 50 mg/ml VEGF Trap Protein (VGFT-SS065)

| Months | Visual Appearance | Turbidity | pH | % VEGF Trap Recovered | % VEGF Trap Native Configuration |
|---|---|---|---|---|---|
| 0 | Pass | 0.00 | 6.2 | 100 | 98.9 |
| 3 | Pass | 0.00 | 6.1 | 104 | 98.5 |
| 6 | Pass | 0.01 | 6.3 | 99 | 98.3 |
| 9 | Pass | 0.00 | 6.3 | 102 | 97.6 |
| 12 | Pass | 0.01 | 6.3 | 103 | 98.0 |
| 18 | Pass | 0.00 | 6.3 | 113 | 97.7 |
| 24 | Pass | 0.00 | 6.2 | 106 | 97.6 |

Example 3. Stability of 40 mg/ml VEGF Trap Liquid Formulation Stored at 5° C. in 3 ml Glass Vials A liquid formulation containing 40 mg/ml VEGF Trap (SEQ ID NO:4), 10 mM phosphate, 40 mM NaCl, 0.03% polysorbate 20, 5% sucrose, and pH 6.3, was stored at 5° C. in 3 ml glass vials and samples tested at 0.5, 1, 2, 3, and 4 months. Stability results are shown in Table 3. Turbidity, percent recovered protein and purity was determined as described above.

TABLE 3

Stability of 40 mg/ml VEGF Trap Protein (VGFT-SS207)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.5 |
| 0.5 | Pass | 0.00 | 6.3 | 99 | 99.4 |
| 1 | Pass | 0.00 | 6.2 | 98 | 99.5 |
| 2 | Pass | 0.00 | 6.2 | 95 | 99.2 |
| 3 | Pass | 0.01 | 6.4 | | |
| 4 | Pass | 0.01 | 6.3 | | |

Example 4. Stability of 40 mg/ml VEGF Trap Liquid Formulation Stored at 5° C. in Pre-Filled Glass Syringe A liquid formulation containing 40 mg/ml VEGF trap (SEQ ID NO:4), 10 mM phosphate, 40 mM NaCl, 0.03% polysorbate 20, 5% sucrose, and pH 6.3, was stored at 5° C. in 1 ml prefilled luer glass syringe with 4023/50 FluroTec coated plunger and samples tested at 0.5, 1, 2, 3, and 4 months. Stability results are shown in Table 4. Turbidity, percent recovered protein and purity was determined as described above.

TABLE 4

Stability of 40 mg/ml VEGF Trap Protein (VGFT-SS207)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.4 |
| 0.5 | Pass | 0.00 | 6.3 | 100 | 99.3 |
| 1 | Pass | 0.00 | 6.3 | 100 | 99.4 |
| 2 | Pass | 0.00 | 6.3 | 97 | 99.1 |
| 3 | Pass | 0.01 | 6.4 | | |
| 4 | Pass | 0.01 | 6.3 | | |

Example 5. Stability of 40 mg/ml VEGF Trap Liquid Formulation Stored at 5° C. in 3 ml Glass Vials A liquid formulation containing 40 mg/ml VEGF trap (SEQ ID NO:4), 10 mM phosphate, 135 mM NaCl, 0.03% polysorbate 20, and pH 6.3, was stored at 5° C. in 3 ml glass vials and samples tested at 0.5, 1, 2, 3, and 4 months. Stability results are shown in Table 5. Turbidity, percent recovered protein and purity was determined as described above.

TABLE 5

Stability of 40 mg/ml VEGF Trap Protein (VGFT-SS203)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.3 |
| 0.5 | Pass | 0.00 | 6.2 | 87 | 99.2 |
| 1 | Pass | 0.00 | 6.2 | 88 | 99.1 |
| 2 | Pass | 0.00 | 6.3 | 103 | 99.2 |
| 3 | Pass | 0.00 | 6.3 | 88 | 99.0 |
| 4 | Pass | 0.00 | 6.2 | 85 | 98.9 |
| 5 | Pass | 0.00 | 6.3 | 84 | 99.0 |

Example 6. Stability of 40 mg/ml VEGF Trap Liquid Formulation Stored at 5° C. in 1 ml Pre-Filled Glass Syringe A liquid formulation containing 40 mg/ml VEGF trap (SEQ ID NO:4), 10 mM phosphate, 135 mM NaCl, 0.03% polysorbate 20, and pH 6.3, was stored at 5° C. in 1 ml prefilled glass luer syringe with 4023/50 FluroTec coated plunger and samples tested at 0.5, 1, 2, 3, 4, and 5 months. Stability results are shown in Table 6. Turbidity, percent recovered protein and purity was determined as described above.

TABLE 6

Stability of 40 mg/ml VEGF Trap Protein (VGFT-SS203)

| Months | Visual Appearance | Turbidity | pH | % VEGF Trap Recovered | % VEGF Trap Native Configuration |
|---|---|---|---|---|---|
| 0 | Pass | 0.00 | 6.3 | 100 | 99.2 |
| 0.5 | Pass | 0.01 | 6.3 | 101 | 99.2 |
| 1 | Pass | 0.00 | 6.3 | 101 | 99.2 |
| 2 | Pass | 0.00 | 6.3 | — | — |
| 3 | Pass | 0.01 | 6.3 | 102 | 99.1 |
| 4 | Pass | 0.01 | 6.3 | 103 | 98.8 |
| 5 | Pass | 0.00 | 6.3 | 99 | 98.9 |

Example 7. Stability of Lyophilized 20 mg/ml VEGF Trap Formulation Stored at 5° C. in 3 ml Glass Vials and Reconstituted to 40 mg/ml 0.8 ml of a liquid formulation containing 20 mg/ml VEGF trap (SEQ ID NO:4), 5 mM phosphate, 20 mM NaCl, 0.015% polysorbate 20, 2.5% sucrose, and pH 6.3, were lyophilized in 3 ml glass vials. Samples were stored at 5° C. and tested at 1, and 2 months. VEGF trap was reconstituted to a final concentration of 40 mg/ml VEGF Trap (final volume of 0.4 ml). Stability results are shown in Table 7 (t=time in months; *=visual appearance; **=reconstitution time). Turbidity, percent recovered protein and purity was determined as described above.

TABLE 7

Stability of Lyophilized 20 mg/ml VEGF Trap Protein (VGFT-SS216)

| t | Vis. App.* | Recon. Time** (min) | Vis. App.* Reconst'd Liquid | Turbidity | pH | % VEGF Trap Recovered | % VEGF Trap Native Config. |
|---|---|---|---|---|---|---|---|
| 0 | Pass | 0.6 | Pass | 0.00 | 6.3 | 100 | 99.5 |
| 1 | Pass | 0.6 | Pass | 0.01 | 6.3 | 106 | 99.4 |
| 2 | Pass | 0.4 | Pass | 0.01 | 6.2 | 103 | 99.3 |

Example 8. Stability of Lyophilized 20 mg/ml VEGF Trap Formulation Stored at 5° C. in 3 ml Glass Vials 0.8 ml of a liquid formulation containing 20 mg/ml VEGF trap (SEQ ID NO:4), 5 mM phosphate, 67.5 mM NaCl, 0.015% polysorbate 20, and pH 6.3, were lyophilized in 3 ml glass vials. Samples were stored at 5° C. and tested at 1, 2, and 3 months. VEGF trap was reconstituted to a final concentration of 40 mg/ml VEGF trap (final volume of 0.4 ml). Stability results are shown in Table 8 (t=time in months; *=visual appearance; **=reconstitution time).

TABLE 8

Stability of Lyophilized 20 mg/ml VEGF Trap Protein (VGFT-SS216)

| t | Vis. App.* | Recon. Time** (min) | Vis. App. Reconst'd Liquid | Turbidity | pH | % VEGF Trap Recovered | % VEGF Trap Native Config. |
|---|---|---|---|---|---|---|---|
| 0 | Pass | 0.7 | Pass | 0.00 | 6.3 | 100 | 99.0 |
| 1 | Pass | 0.7 | Pass | 0.01 | 6.2 | 105 | 98.9 |
| 2 | Pass | 0.4 | Pass | 0.01 | 6.2 | 103 | 98.9 |

We claim:

1. A liquid ophthalmic formulation comprising:
   40 mg/ml of a glycosylated vascular endothelial growth factor (VEGF) antagonist fusion protein comprising amino acids 27-457 of SEQ ID NO: 4;
   water;
   an organic co-solvent comprising polysorbate; and
   a stabilizing agent,
   wherein the liquid ophthalmic formulation has a pH of between 5.8 to 7.0,
   wherein the liquid ophthalmic formulation is suitable for intravitreal administration,
   wherein 90% or more of the weight of the VEGF antagonist fusion protein is not present as an aggregate, and
   wherein the VEGF antagonist fusion protein is at least 95% free of protein contaminants.

2. The liquid ophthalmic formulation of claim 1, wherein the polysorbate is polysorbate 80, and wherein the stabilizing agent is sucrose and trehalose.

3. The liquid ophthalmic formulation of claim 2, wherein the liquid ophthalmic formulation comprises 0.01% to 3% polysorbate 80.

4. The liquid ophthalmic formulation of claim 3, wherein the liquid ophthalmic formulation comprises 0.03% to 0.1% polysorbate 80.

5. The liquid ophthalmic formulation of claim 4, wherein the liquid ophthalmic formulation comprises 0.1% polysorbate 80.

6. The liquid ophthalmic formulation of claim 4, wherein the liquid ophthalmic formulation comprises 0.03% polysorbate 80.

7. The liquid ophthalmic formulation of claim 2, wherein the liquid ophthalmic formulation comprises 1.0% to 7.5% stabilizing agent.

8. The liquid ophthalmic formulation of claim 2, wherein the liquid ophthalmic formulation comprises 1.0% to 7.5% sucrose.

9. The liquid ophthalmic formulation of claim 8, wherein the liquid ophthalmic formulation comprises 5% sucrose.

10. The liquid ophthalmic formulation of claim 1, wherein the liquid ophthalmic formulation has a pH of between 6.2 to 6.3.

11. A liquid ophthalmic formulation comprising:
40 mg/ml of a glycosylated vascular endothelial growth factor (VEGF) antagonist fusion protein comprising amino acids 27-457 of SEQ ID NO: 4;
water;
an organic co-solvent comprising polysorbate; and
a stabilizing agent,
wherein the liquid ophthalmic formulation has a pH of between 5.8 to 7.0,
wherein the liquid ophthalmic formulation is suitable for intravitreal administration,
wherein at least 98% of the VEGF antagonist fusion protein is present in native conformation following storage at 5° C. for two months as measured by size exclusion chromatography.

12. The liquid ophthalmic formulation of claim 11, wherein the polysorbate is polysorbate 80, and wherein the stabilizing agent is sucrose and trehalose.

13. The liquid ophthalmic formulation of claim 12, wherein the liquid ophthalmic formulation comprises 0.01% to 3% polysorbate 80.

14. The liquid ophthalmic formulation of claim 13, wherein the liquid ophthalmic formulation comprises 0.03% to 0.1% polysorbate 80.

15. The liquid ophthalmic formulation of claim 14, wherein the liquid ophthalmic formulation comprises 0.1% polysorbate 80.

16. The liquid ophthalmic formulation of claim 14, wherein the liquid ophthalmic formulation comprises 0.03% polysorbate 80.

17. The liquid ophthalmic formulation of claim 16, wherein at least 99% of the VEGF antagonist fusion protein is present in native conformation after 2 month storage at 5° C. as measured by size exclusion chromatography.

18. The liquid ophthalmic formulation of claim 12, wherein the liquid ophthalmic formulation comprises 1.0% to 7.5% stabilizing agent.

19. The liquid ophthalmic formulation of claim 12, wherein the liquid ophthalmic formulation comprises 1.0% to 7.5% sucrose.

20. The liquid ophthalmic formulation of claim 19, wherein the liquid ophthalmic formulation comprises 5% sucrose.

21. The liquid ophthalmic formulation of claim 11, wherein the liquid ophthalmic formulation has a pH of between 6.2 to 6.3.

22. A liquid ophthalmic formulation comprising:
40 mg/ml of a glycosylated vascular endothelial growth factor (VEGF) antagonist fusion protein comprising amino acids 27-457 of SEQ ID NO: 4;
water;
an organic co-solvent comprising polysorbate 80; and
a stabilizing agent comprising sucrose and trehalose,
wherein the liquid ophthalmic formulation has a pH of about 6.2 to 6.3,
wherein the liquid ophthalmic formulation is suitable for intravitreal administration,
wherein 90% or more of the weight of the VEGF antagonist fusion protein is not present as an aggregate, and
wherein the VEGF antagonist fusion protein is at least 95% free of protein contaminants.

23. The liquid ophthalmic formulation of claim 22, wherein the liquid ophthalmic formulation comprises 0.01% to 3% polysorbate 80.

24. The liquid ophthalmic formulation of claim 22, wherein the liquid ophthalmic formulation comprises 1.0% to 7.5% stabilizing agent.

25. The liquid ophthalmic formulation of claim 22, wherein the liquid ophthalmic formulation comprises 1.0% to 7.5% sucrose.

26. A liquid ophthalmic formulation comprising:
40 mg/ml of a glycosylated vascular endothelial growth factor (VEGF) antagonist fusion protein comprising amino acids 27-457 of SEQ ID NO: 4;
water;
an organic co-solvent comprising polysorbate 80; and
a stabilizing agent comprising sucrose and trehalose,
wherein the liquid ophthalmic formulation has a pH of about 6.2 to 6.3,
wherein the liquid ophthalmic formulation is suitable for intravitreal administration,
wherein at least 98% of the VEGF antagonist fusion protein is present in native conformation following storage at 5° C. for two months as measured by size exclusion chromatography.

27. The liquid ophthalmic formulation of claim 26, wherein the liquid ophthalmic formulation comprises 0.01% to 3% polysorbate 80.

28. The liquid ophthalmic formulation of claim 27, wherein the liquid ophthalmic formulation comprises 0.03% polysorbate 80, and wherein at least 99% of the VEGF antagonist fusion protein is present in native conformation after 2 month storage at 5° C. as measured by size exclusion chromatography.

29. The liquid ophthalmic formulation of claim 26, wherein the liquid ophthalmic formulation comprises 1.0% to 7.5% stabilizing agent.

30. The liquid ophthalmic formulation of claim 26, wherein the liquid ophthalmic formulation comprises 1.0% to 7.5% sucrose.

* * * * *

```
                        SEQUENCE LISTING

Sequence total quantity: 4
SEQ ID NO: 1            moltype = DNA  length = 1453
FEATURE                 Location/Qualifiers
misc_feature            1..1453
                        note = synthetic
source                  1..1453
                        mol_type = other DNA
                        organism = synthetic construct
SEQUENCE: 1
aagcttgggc tgcaggtcga tcgactctag aggatcgatc cccggcgag ctcgaattcg   60
caaccaccat ggtcagctac tgggacaccg gggtcctgct gtgcgcgctg ctcagctgtc  120
tgcttctcac aggatctagt tccggaggta gacctttcgt agagatgtac agtgaaatcc  180
ccgaaattat acacatgact gaaggaaggg agctcgtcat tccctgccgg gttacgtcac  240
ctaacatcac tgttacttta aaaaagtttc cacttgacac tttgatccct gatggaaaac  300
gcataatctg ggacagtaga aagggcttca tcatatcaaa tgcaacgtac aaagaaatag  360
ggcttctgac ctgtgaagca acagtcaatg gcatttgta taagacaaac tatctcacac  420
atcgacaaac caatacaatc atagatgtgg ttctgagtcc gtctcatgga attgaactat  480
ctgttggaga aaagcttgtc ttaaattgta gcagcaagaac tgaactaaat gtggggattg  540
acttcaactg gaatacccct tcttcgaagc atcagcataa gaaacttgta aaccgagacc  600
taaaaaccca gtctgggagt gagatgaaga aattttttgag caccttaact atagatggtg  660
taaccggag tgaccaagga ttgtacacct gtgcagcatc cagtgggctg atgaccaaga  720
agaacagcac atttgtcagg gtccatgaaa agggcccggg cgacaaaact cacacatgcc  780
caccgtgccc agcacctgaa ctcctggggg gaccgtcagt cttcctcttc ccccaaaac   840
ccaaggacac cctcatgatc tcccggaccc ctgaggtcac atgcgtggtg gtggacgtga  900
gccacgaaga ccctgaggtc aagttcaact ggtacgtgga cggcgtggag gtgcataatg  960
ccaagacaaa gccgcgggag gagcagtaca acagcacgta ccgtgtggtc agcgtcctca 1020
ccgtcctgca ccaggactgg ctgaatggca aggagtacaa gtgcaaggtc tccaacaaag 1080
ccctcccagc ccccatcgag aaaaccatct ccaaagccaa agggcagccc cgagaaccac 1140
aggtgtacac cctgccccca tcccgggatg agctgaccaa gaaccaggtc agcctgacct 1200
gcctggtcaa aggcttctat cccagcgaca tcgccgtgga gtgggagagc aatgggcagc 1260
cggagaacaa ctacaagacc acgcctcccg tgctggactc cgacggctcc ttcttcctct 1320
atagcaagct caccgtggac aagagcaggt ggcagcaggg gaacgtcttc tcatgctccg 1380
tgatgcatga ggctctgcac aaccactaca cgcagaagag cctctccctg tctccgggta 1440
aatgagcggc cgc                                                    1453

SEQ ID NO: 2            moltype = AA  length = 458
FEATURE                 Location/Qualifiers
REGION                  1..458
                        note = synthetic
source                  1..458
                        mol_type = protein
                        organism = synthetic construct
SEQUENCE: 2
```

```
MVSYWDTGVL LCALLSCLLL TGSSSGGRPF VEMYSEIPEI IHMTEGRELV IPCRVTSPNI  60
TVTLKKFPLD TLIPDGKRII WDSRKGFIIS NATYKEIGLL TCEATVNGHL YKTNYLTHRQ 120
TNTIIDVVLS PSHGIELSVG EKLVLNCTAR TELNVGIDFN WEYPSSKHQH KKLVNRDLKT 180
QSGSEMKKFL STLTIDGVTR SDQGLYTCAA SSGLMTKKNS TFVRVHEKGP GDKTHTCPPC 240
PAPELLGGPS VFLFPPKPKD TLMISRTPEV TCVVVDVSHE DPEVKFNWYV DGVEVHNAKT 300
KPREEQYNST YRVVSVLTVL HQDWLNGKEY KCKVSNKALP APIEKTISKA KGQPREPQVY 360
TLPPSRDELT KNQVSLTCLV KGFYPSDIAV EWESNGQPEN NYKTTPPVLD SDGSFFLYSK 420
LTVDKSRWQQ GNVFSCSVMH EALHNHYTQK SLSLSPGK                        458

SEQ ID NO: 3           moltype = DNA  length = 1377
FEATURE                Location/Qualifiers
misc_feature           1..1377
                       note = synthetic
source                 1..1377
                       mol_type = other DNA
                       organism = synthetic construct
SEQUENCE: 3
atggtcagct actgggacac cggggtcctg ctgtgcgcgc tgctcagctg tctgcttctc   60
acaggatcta gttccggaag tgataccggt agacctttcg tagagatgta cagtgaaatc  120
cccgaaatta tacacatgac tgaaggaagg gagctcgtca ttccctgccg ggttacgtca  180
cctaacatca ctgttacttt aaaaaagttt ccacttgaca ctttgatccc tgatggaaaa  240
cgcataatct gggacagtag aaagggcttc atcatatcaa atgcaactga caaagaaata  300
gggcttctga cctgtgaagc aacagtcaat gggcatttgt ataagacaaa ctatctcaca  360
catcgacaaa ccaatacaat catagatgtg gttctgagtc cgtctcatgg aattgaacta  420
tctgttggag aaaagcttgt cttaaattgt acagcaagaa ctgaactaaa tgtgggatt   480
gacttcaact gggaataccc ttcttcgaag catcagcata gaaaacttgt aaaccgagac  540
ctaaaaaccc agtctgggag tgagatgaag aattttttga gcaccttaac tatagatggt  600
gtaacccgga gtgaccaagg attgtacacc tgtgcagcat ccagtgggct gatgaccaag  660
aagaacagca catttgtcag ggtccatgaa aaggacaaaa ctcacacatg cccaccgtgc  720
ccagcaccta aactcctggg ggaccgtca gtcttcctct ccccccaaa acccaaggac   780
accctcatga tctccggac ccctgaggtc acatgcgtgg tggtggacgt gagccacgaa  840
gaccctgagg tcaagttcaa ctggtacgtg gacggcgtgg aggtgcataa tgccaagaca  900
aagccgcggg aggagcagta caacagcacg taccgtgtgg tcagcgtcct caccgtcctg  960
caccaggact ggctgaatgg caaggagtac aagtgcaagg tctccaacaa agccctccca 1020
gcccccatcg agaaaaccat ctccaaagcc aaagggcagc cccgagaacc acaggtgtac 1080
accctgcccc catcccggga tgagctgacc aagaaccagg tcagcctgac ctgcctggtc 1140
aaaggcttct atcccagcga catcgccgtg gagtgggaga gcaatgggca gccggagaac 1200
aactacaaga ccacgcctcc cgtgctggac tccgacggct ccttcttcct ctacagcaag 1260
ctcaccgtgg acaagagcag gtggcagcag gggaacgtct tctcatgctc cgtgatgcat 1320
gaggctctgc acaaccacta cacgcagaag agcctctccc tgtctccggg taaatga    1377

SEQ ID NO: 4           moltype = AA  length = 458
FEATURE                Location/Qualifiers
REGION                 1..458
                       note = synthetic
source                 1..458
                       mol_type = protein
                       organism = synthetic construct
SEQUENCE: 4
MVSYWDTGVL LCALLSCLLL TGSSSGSDTG RPFVEMYSEI PEIIHMTEGR ELVIPCRVTS  60
PNITVTLKKF PLDTLIPDGK RIIWDSRKGF IISNATYKEI GLLTCEATVN GHLYKTNYLT 120
HRQTNTIIDV VLSPSHGIEL SVGEKLVLNC TARTELNVGI DFNWEYPSSK HQHKKLVNRD 180
LKTQSGSEMK KFLSTLTIDG VTRSDQGLYT CAASSGLMTK KNSTFVRVHE KDKTHTCPPC 240
PAPELLGGPS VFLFPPKPKD TLMISRTPEV TCVVVDVSHE DPEVKFNWYV DGVEVHNAKT 300
KPREEQYNST YRVVSVLTVL HQDWLNGKEY KCKVSNKALP APIEKTISKA KGQPREPQVY 360
TLPPSRDELT KNQVSLTCLV KGFYPSDIAV EWESNGQPEN NYKTTPPVLD SDGSFFLYSK 420
LTVDKSRWQQ GNVFSCSVMH EALHNHYTQK SLSLSPGK                        458
```